United States Patent
Bowen et al.

(10) Patent No.: US 8,778,849 B2
(45) Date of Patent: Jul. 15, 2014

(54) MICROARRAY FABRICATION SYSTEM AND METHOD

(71) Applicant: Illumina, Inc., San Diego, CA (US)

(72) Inventors: M. Shane Bowen, La Jolla, CA (US); Kevin L. Gunderson, Encinitas, CA (US); Shengrong Lin, Fremont, CA (US); Maria Candelaria Rogert Bacigalupo, Cardiff by the Sea, CA (US); Kandaswamy Vijayan, San Diego, CA (US); Yir-Shyuan Wu, Albany, CA (US); Bala Murali Venkatesan, San Diego, CA (US); James Tsay, San Diego, CA (US); John M. Beierle, Laguna Niguel, CA (US); Lorenzo Berti, San Diego, CA (US); Sang Ryul Park, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/661,524

(22) Filed: Oct. 26, 2012

(65) Prior Publication Data

US 2013/0116153 A1    May 9, 2013

Related U.S. Application Data

(60) Provisional application No. 61/552,712, filed on Oct. 28, 2011.

(51) Int. Cl.
*C40B 50/18* (2006.01)
*C40B 40/06* (2006.01)
*C40B 50/00* (2006.01)
*C40B 50/14* (2006.01)

(52) U.S. Cl.
USPC .................. 506/32; 506/16; 506/23; 506/30

(58) Field of Classification Search
CPC ............. B01J 2219/00529; B01J 2219/00608; C40B 40/06; C40B 50/00; C40B 50/14; C40B 50/18
USPC ......................................... 506/16, 23, 30, 32
See application file for complete search history.

(56) References Cited

U.S. PATENT DOCUMENTS

| | | |
|---|---|---|
| 5,324,633 A | 6/1994 | Fodor et al. |
| 5,429,807 A | 7/1995 | Matson et al. |

(Continued)

FOREIGN PATENT DOCUMENTS

| | | |
|---|---|---|
| EP | 0868530 B1 | 4/2003 |
| EP | 2302028 A1 | 3/2011 |

(Continued)

OTHER PUBLICATIONS

Barbee et al., "Fabrication of DNA Polymer Brush Arrays by Destructive Micropatterning and Rolling-Circle Amplification," Macromol. Biosci. 2011, 11:607-617, published online on Feb. 8, 2011.*

(Continued)

*Primary Examiner* — Samuel Woolwine
*Assistant Examiner* — Kaijiang Zhang
(74) *Attorney, Agent, or Firm* — Fletcher, Yoder, P.C.

(57) ABSTRACT

A microarray is designed capture one or more molecules of interest at each of a plurality of sites on a substrate. The sites comprise base pads, such as polymer base pads, that promote the attachment of the molecules at the sites. The microarray may be made by one or more patterning techniques to create a layout of base pads in a desired pattern. Further, the microarrays may include features to encourage clonality at the sites.

18 Claims, 29 Drawing Sheets

(56) References Cited

U.S. PATENT DOCUMENTS

| | | | |
|---|---|---|---|
| 5,436,327 A | 7/1995 | Southern et al. |
| 5,451,683 A | 9/1995 | Barrett et al. |
| 5,482,867 A | 1/1996 | Barrett et al. |
| 5,491,074 A | 2/1996 | Aldwin et al. |
| 5,561,071 A | 10/1996 | Hollenberg et al. |
| 5,583,211 A | 12/1996 | Coassin et al. |
| 5,599,675 A | 2/1997 | Brenner |
| 5,624,711 A | 4/1997 | Sundberg et al. |
| 5,641,658 A | 6/1997 | Adams et al. |
| 5,658,734 A | 8/1997 | Brock et al. |
| 5,744,305 A | 4/1998 | Fodor et al. |
| 5,750,341 A | 5/1998 | Macevicz |
| 5,772,905 A | 6/1998 | Chou |
| 5,795,716 A | 8/1998 | Chee et al. |
| 5,831,070 A | 11/1998 | Pease et al. |
| 5,837,858 A | 11/1998 | Brennan |
| 5,856,101 A | 1/1999 | Hubbell et al. |
| 5,858,659 A | 1/1999 | Sapolsky et al. |
| 5,871,921 A | 2/1999 | Landegren et al. |
| 5,874,219 A | 2/1999 | Rava et al. |
| 5,919,523 A | 7/1999 | Sundberg et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,022,963 A | 2/2000 | McGall et al. |
| 6,025,601 A | 2/2000 | Trulson et al. |
| 6,033,860 A | 3/2000 | Lockhart et al. |
| 6,083,697 A | 7/2000 | Beecher et al. |
| 6,090,555 A | 7/2000 | Fiekowsky et al. |
| 6,124,120 A | 9/2000 | Lizardi |
| 6,136,269 A | 10/2000 | Winkler et al. |
| 6,210,891 B1 | 4/2001 | Nyren et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,287,768 B1 | 9/2001 | Chenchik et al. |
| 6,288,220 B1 | 9/2001 | Kambara et al. |
| 6,291,183 B1 | 9/2001 | Pirrung et al. |
| 6,291,193 B1 | 9/2001 | Khodadoust |
| 6,297,006 B1 | 10/2001 | Drmanac et al. |
| 6,309,831 B1 | 10/2001 | Goldberg et al. |
| 6,355,431 B1 | 3/2002 | Chee et al. |
| 6,416,949 B1 | 7/2002 | Dower et al. |
| 6,428,752 B1 | 8/2002 | Montagu |
| 6,432,360 B1 | 8/2002 | Church |
| 6,465,178 B2 | 10/2002 | Chappa et al. |
| 6,482,591 B2 | 11/2002 | Lockhart et al. |
| 6,489,606 B1 | 12/2002 | Kersey et al. |
| 6,514,751 B2 | 2/2003 | Johann et al. |
| 6,737,236 B1 | 5/2004 | Pieken et al. |
| 6,770,441 B2 | 8/2004 | Dickinson et al. |
| 6,859,570 B2 | 2/2005 | Walt et al. |
| 6,890,741 B2 | 5/2005 | Fan et al. |
| 6,913,884 B2 | 7/2005 | Stuelpnagel et al. |
| 6,932,934 B2 | 8/2005 | Choi et al. |
| 6,986,989 B2 | 1/2006 | Mirkin et al. |
| 7,001,792 B2 | 2/2006 | Sauer et al. |
| 7,019,835 B2 | 3/2006 | McMackin et al. |
| 7,057,026 B2 | 6/2006 | Barnes et al. |
| 7,106,513 B2 | 9/2006 | Moon et al. |
| 7,115,400 B1 | 10/2006 | Adessi et al. |
| 7,122,482 B2 | 10/2006 | Xu et al. |
| 7,126,755 B2 | 10/2006 | Moon et al. |
| 7,140,861 B2 | 11/2006 | Watts et al. |
| 7,164,533 B2 | 1/2007 | Moon et al. |
| 7,186,656 B2 | 3/2007 | Sreenivasan |
| 7,205,244 B2 | 4/2007 | Stacey et al. |
| 7,211,414 B2 | 5/2007 | Hardin et al. |
| 7,244,559 B2 | 7/2007 | Rothberg et al. |
| 7,259,258 B2 | 8/2007 | Kozlov et al. |
| 7,279,113 B2 | 10/2007 | Watts et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,375,234 B2 | 5/2008 | Sharpless et al. |
| 7,405,281 B2 | 7/2008 | Xu et al. |
| 7,427,678 B2 | 9/2008 | Pieken et al. |
| 7,547,504 B2 | 6/2009 | Sreenivasan |
| 7,582,420 B2 | 9/2009 | Oliphant et al. |
| 7,595,883 B1 | 9/2009 | El Gamal et al. |
| 7,597,932 B2 | 10/2009 | Krotz et al. |
| 7,635,445 B2 | 12/2009 | Choi et al. |
| 7,785,526 B2 | 8/2010 | Voisin |
| 7,785,790 B1 | 8/2010 | Church et al. |
| 7,813,013 B2 | 10/2010 | Kain |
| 7,837,921 B2 | 11/2010 | Xu et al. |
| 2002/0012930 A1 | 1/2002 | Rothberg et al. |
| 2002/0055100 A1 | 5/2002 | Kawashima et al. |
| 2003/0059929 A1 | 3/2003 | Heller et al. |
| 2003/0108867 A1 | 6/2003 | Chee et al. |
| 2003/0108900 A1 | 6/2003 | Oliphant et al. |
| 2003/0170684 A1 | 9/2003 | Fan |
| 2003/0207295 A1 | 11/2003 | Gunderson et al. |
| 2003/0215937 A1 | 11/2003 | Matson |
| 2004/0002090 A1 | 1/2004 | Mayer et al. |
| 2004/0096853 A1 | 5/2004 | Mayer |
| 2005/0053980 A1 | 3/2005 | Gunderson et al. |
| 2005/0181394 A1 | 8/2005 | Steemers et al. |
| 2005/0181440 A1 | 8/2005 | Chee et al. |
| 2005/0191698 A1 | 9/2005 | Chee et al. |
| 2005/0227252 A1 | 10/2005 | Moon et al. |
| 2006/0006327 A1 | 1/2006 | Donaldson et al. |
| 2006/0023310 A1 | 2/2006 | Putnam et al. |
| 2006/0071075 A1 | 4/2006 | Moon et al. |
| 2006/0102471 A1 | 5/2006 | Maurer et al. |
| 2006/0119913 A1 | 6/2006 | Moon |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0038718 A1 | 2/2008 | Fischer |
| 2008/0108082 A1 | 5/2008 | Rank et al. |
| 2009/0026082 A1 | 1/2009 | Rothberg et al. |
| 2009/0111169 A1 | 4/2009 | Kim et al. |
| 2009/0127589 A1 | 5/2009 | Rothberg et al. |
| 2009/0186349 A1 | 7/2009 | Gunderson et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2011/0059865 A1 | 3/2011 | Smith et al. |
| 2011/0105366 A1 | 5/2011 | Lebi et al. |
| 2011/0111984 A1 | 5/2011 | Nakatani et al. |
| 2011/0220775 A1 | 9/2011 | Triener et al. |
| 2012/0020537 A1 | 1/2012 | Garcia et al. |
| 2012/0152742 A1* | 6/2012 | Gorfinkel et al. ............ 204/452 |
| 2012/0270305 A1 | 10/2012 | Reed et al. |
| 2012/0316086 A1 | 12/2012 | Lin |

FOREIGN PATENT DOCUMENTS

| | | |
|---|---|---|
| WO | WO 89/10977 | 11/1989 |
| WO | WO 91/06678 | 5/1991 |
| WO | WO 93/17126 | 9/1993 |
| WO | WO 95/35505 | 12/1995 |
| WO | WO 00/31148 | 6/2000 |
| WO | WO 00/53812 | 9/2000 |
| WO | WO 00/63437 | 10/2000 |
| WO | WO 01/01143 | 1/2001 |
| WO | 0162982 A2 | 8/2001 |
| WO | WO 03/014392 | 2/2003 |
| WO | 03049677 A2 | 6/2003 |
| WO | WO 2004/018497 | 3/2004 |
| WO | WO 2004/024328 | 3/2004 |
| WO | WO 2005/033681 | 4/2005 |
| WO | WO 2007/123744 | 11/2007 |
| WO | WO 2008157640 A2 * | 12/2008 |

OTHER PUBLICATIONS

U.S. Appl. No. 61/438,486, filed Feb. 1, 2011, Mark Reed.
U.S. Appl. No. 13/267,565, filed Oct. 6, 2011, Jason Harris.
U.S. Appl. No. 61/657,508, filed Jun. 8, 2012, Wayne N. George.
U.S. Appl. No. 61/660,487, filed Jun. 15, 2012, Min-Jui Richard Shen.

(56) References Cited

OTHER PUBLICATIONS

U.S. Appl. No. 61/715,478, filed Oct. 18, 2012, Min-Jui Richard Shen.
Bains et al., "A Novel Method for Nucleic Acid Sequence Determination", Journal of Theoretical Biology 135(3), 303-7 (1988).
Bentley et al., "Accurate whole human genome sequencing using reversible terminator chemistry", Nature 456:53-59 (2008).
Cockroft, et al., "A Single-Molecule Nanopore Device Detects DNA Polymerase Activity With Single-Nucleotide Resolution", *J. Am. Chem. Soc.* 130, 818-820 (2008).
Drmanac et al., "Accurate squencing by hybridization for DNA diagnostics and individual genomics", Nature Biotechnology 16, 54-58 (1998).
Fodor et al., "Light-Directed, Spatially Addressable Parallel Chemical Synthesis", *Science* 251(4995), 767-773 (1995).
Healy, "Nanopore-based single-molecule DNA analysis", *Nanomed.* 2, 459-481 (2007).
Korlach et al., "Selective aluminum passivation for targeted immobilization of single DNA polymerase molecules in zero-mode waveguide nanostructures", *Proc. Natl. Acad. Sci. A* 105, 1176-1181 (2008).
Levene et al., "Zero-Mode Waveguides for Single-Molecule Analysis at High Concentrations," *Science* 299, 682-686 (2003).
Lizardi et al., "Mutation detection and single-molecule counting using isothermal rolling-circle amplification," *Nat. Genet.* 19:225-232 (1998).
Lundquist et al., "Parallel confocal detection of single molecules in real time", *Opt. Lett.* 33, 1026-1028 (2008).
Ronaghi, et al., "Real-Time DNA Sequencing Using Detection of Pyrophosphate Release", *Analytical Biochemistry* 242(1), 84-9 (1996).
Ronaghi et al., "A Sequencing Method Based on Real-Time Pyrophosphate", *Science* 281(5375), 363 (1998).
Ronaghi, "Pyrosequencing Sheds Light on DNA Sequencing", *Genome Res.* 11(1), 3-11 (2001).
Shendure et al., "Accurate Multiplex Polony Sequencing of an Evolved Bacterial Genome," *Science* 309:1728-1732 (2005).
Soni & Meller, "Progress toward Ultrafast DNA Sequencing Using Solid-State Nanopores", *Clin. Chem.* 53, 1996-2001 (2007).
Thornton, "High Rate Thick Film Growth", Ann. Rev. Mater. Sci. 7:239-60 (1977).
Reed et al., File History U.S. Appl. No. 61/438,486, filed Feb. 1, 2011, Systems and Methods and Apparatuses to Image a Sample for Biological or Chemical Analysis.
Harris et al., File History U.S. Appl. No. 13/267,565, filed Oct. 6, 2011, Array Domains Having Rotated Patterns.
George et al., File History U.S. Appl. No. 61/657,508, filed Jun. 8, 2012, Polymer Coatings.
Shen et al., File History U.S. Appl. No. 61/660,487 filed Jun. 15, 2012, Kinetic Exclusion Amplification of Nucleic Acid Libraries.
Shen et al., File History U.S. Appl. No. 61/715,478, filed Oct. 18, 2012, Kinetic Exclusion Amplification of Nucleic Acid Libraries.
Lin et al., U.S. Appl. No. 13/492,661, filed Jun. 8, 2012, Patterned Flow Cells Useful for Nucleic Acid Analysis.
Partial International Search Report for application No. PCT/US2012/062105 mailed May 6, 2013.

\* cited by examiner

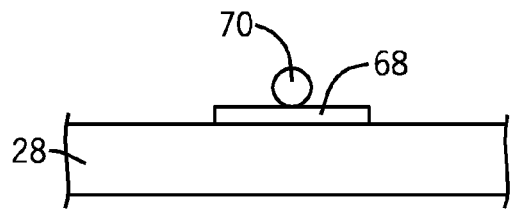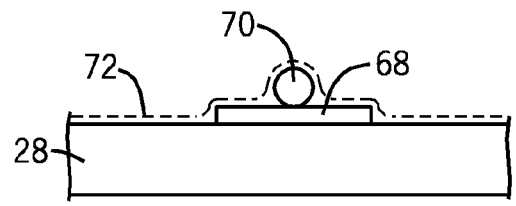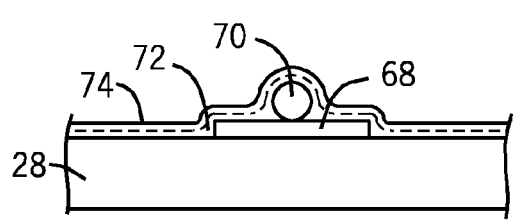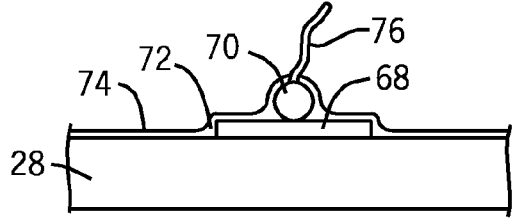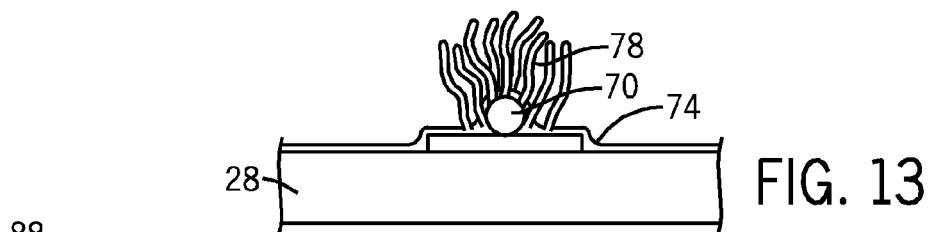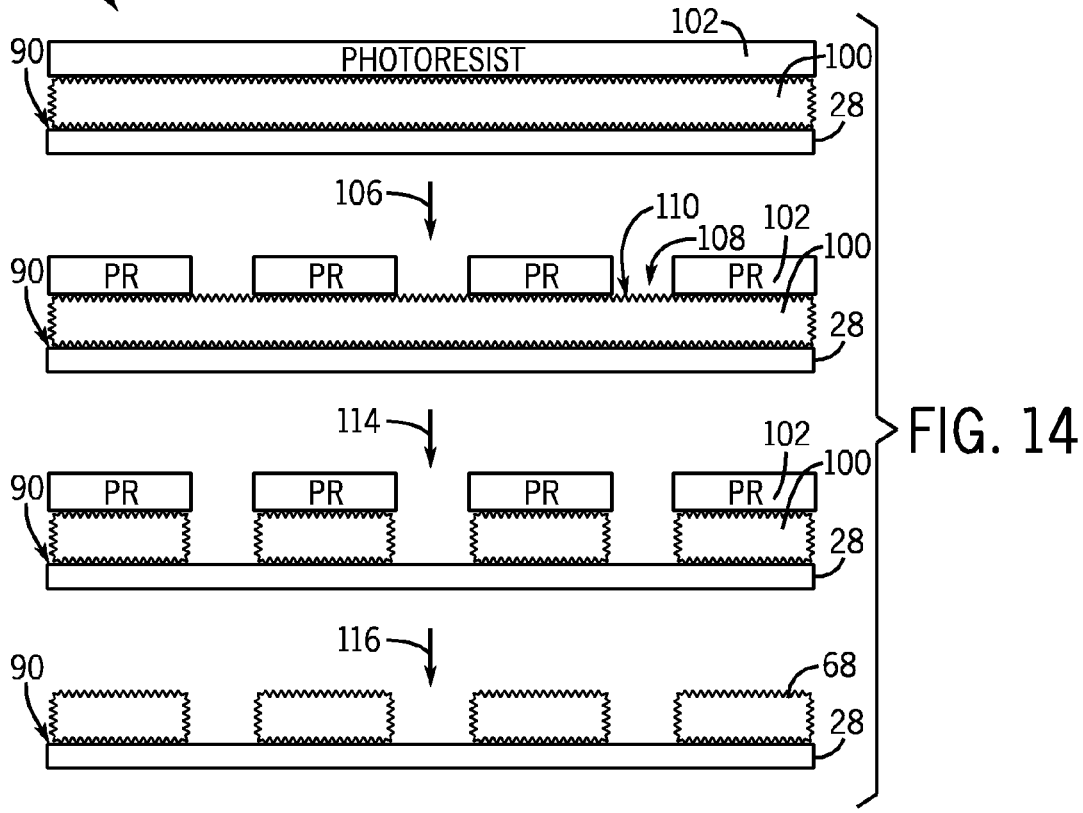

MICROARRAY FABRICATION SYSTEM AND METHOD

CROSS-REFERENCE TO RELATED APPLICATIONS

This application claims priority to U.S. Provisional Patent Application No. 61/552,712, entitled "SINGLE MOLECULE MICROARRAY SYSTEM AND METHOD," filed Oct. 28, 2011, which is herein incorporated in its entirety by reference for all purposes.

BACKGROUND

The invention relates generally to the field of microarrays used for detecting and analyzing molecules of interest, particularly biological materials.

Biological microarrays have become a key mechanism in a wide range of tools used to detect and analyze molecules, including deoxyribonucleic acid (DNA) and ribonucleic acid (RNA). In these applications, the microarrays are engineered to include probes for these nucleotide sequences present in genes in humans and other organisms. In certain applications, for example, individual DNA and RNA probes may be attached at small locations in a geometric grid (or randomly) on a microarray support. A test sample, such as from a known person or organism, may be exposed to the grid, such that complimentary genes of fragments hybridize to probes at the individual sites in the array. The array can then be examined by scanning specific frequencies of light over the sites to identify which genes or fragments in the sample are present, by fluorescence of the sites at which genes or fragments hybridized.

In similar applications, biological microarrays may be used for genetic sequencing and similar applications. In general, genetic sequencing consists of determining the order of nucleotides or nucleic acid in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of much more extensive lengths of genetic material from which the fragments were derived. Automated, computer-based examination of characteristic fragments have been developed, and have been used more recently in genome mapping, identification of genes and their function, evaluation of risks of certain conditions and disease states, and so forth. Beyond these applications, such microarrays may be used for the detection and evaluation of a wide range of molecules, families of molecules, genetic expression levels, single nucleotide polymorphisms, and genotyping.

For these and other applications of biological microarrays, improvements have recently been made in imaging systems for capturing data related to the individual molecules attached at sites of the microarrays. For example, improvements in imaging systems allow for faster, more accurate and higher resolution scanning and imaging, particularly through the use of line-scanning and confocal control of imaging optics. However, as the density of microarrays increases, and the size of the areas containing individually characterized sites also increases, scanning, both by point scanning and line scanning approaches becomes problematic. In particular, there is a continuous drive in the field for more densely packed arrays that can hold more molecular information on a given support (capable of being analyzed in a single text). This packing density poses challenges for both processing and imaging. Moreover, it would be beneficial to provide a high degree of uniformity in the molecules attached at each site of the arrays, such that better signal-to-noise ratios are obtained for the individual sites. Current techniques for creating, preparing and utilizing the microarrays are in need of improvement if further density and signal-to-noise improvements are to be realized.

BRIEF DESCRIPTION

Embodiments of the present disclosure include a method for preparing a biological microarray. The steps of the method include forming an array of base pads at predetermined sites on a substrate, wherein individual base pads are configured to capture a nucleic acid molecule; disposing a nucleic acid molecule capture substance over each of the base pads; and disposing a porous attachment layer over the base pads, wherein the porous attachment layer is configured to attach amplified copies of the nucleic acid molecules.

Embodiments of the present disclosure include a method for preparing a biological microarray. The steps of the method include providing an array of base pads at predetermined sites on a substrate, wherein individual base pads are configured to capture a nucleic acid molecule; and contacting the array of base pads with a mixture of different nucleic acid molecules under conditions wherein a nucleic acid molecule is captured at each base pad, wherein a porous attachment layer is disposed over the base pads and the porous attachment layer is configured to attach amplified copies of the nucleic acid molecules comprising nucleotides or nucleotide-like components.

Embodiments of the present disclosure include a method for preparing a biological microarray. The steps of the method include forming an array of base pads at predetermined sites on a substrate; disposing a molecule binding substance over each of the base pads, thereby configuring each of the base pads to capture a nucleic acid molecule; disposing a porous attachment layer over the base pads; seeding each of the base pads with a single nucleic acid molecule by linking the single nucleic acid molecule to the molecule binding substance; and amplifying the nucleic acid molecule at each base pad to obtain at each base pad a region comprising copies of the nucleic acid molecule, wherein the copies of the nucleic acid molecule are attached to the porous attachment layer.

Embodiments of the present disclosure include a biological microarray system that includes an array of base pads at predetermined sites on a substrate; a molecule binding substance disposed over each of the base pads configured to capture a nucleic acid molecule at each of the base pads; and a porous attachment layer disposed over the base pads, wherein the porous attachment layer is configured to attach amplified copies of the nucleic acid molecules.

Embodiments of the present disclosure include a biological microarray system that includes an array of base pads at predetermined sites on a substrate; a molecule binding substance disposed over each of the base pads and linked to no more than a nucleic acid molecule; a porous attachment layer disposed over the base pads; and several copies of each of the nucleic acid molecules linked to the porous attachment layer disposed over each of the respective base pads.

Embodiments of the present disclosure include a method for preparing a biological microarray. The steps of the method include forming a polymer layer on a substrate; disposing a photoresist layer over the polymer layer; forming interstitial spaces in the photoresist layer and the polymer layer; removing the photoresist layer to expose polymer base pads, wherein the polymer base pads are coupled to a molecule binding substance. The polymer layer may include a poly(N-(5-azidoacetamidylpentyl)acrylamide-co-acrylamide) polymer.

Embodiments of the present disclosure include a method for preparing a biological microarray. The steps of the method include activating regions on a substrate to form a pattern of activated regions; contacting the substrate with a self-assembling monomer solution; polymerizing the monomers to form polymer base pads only on the activated regions wherein the polymer base pads are coupled to a molecule binding substance.

Embodiments of the present disclosure include a method for preparing a biological microarray. The steps of the method include coupling amine groups to a surface of a microarray substrate with a silylation reagent; coupling the amine groups to N-hydroxysulfosuccinimidyl-4-azidobenzoate; exposing the N-hydroxysulfosuccinimidyl-4-azidobenzoate to light such that a nitrene is generated; reacting the nitrene with poly(N-(5-azidoacetamidylpentyl)acrylamide-co-acrylamide) monomers; and cross-linking the poly(N-(5-azidoacetamidylpentyl)acrylamide-co-acrylamide) monomers to form a polymer. As an alternative to silylation reagent, polylysine or polyethyleneimine can be used.

Embodiments of the present disclosure include a biological microarray system that includes an array of base pads at predetermined sites on a substrate; a molecule binding substance disposed over each of the base pads; and a passivation layer disposed on the substrate between base pads. The passivation layer may include diamond-like carbon, hexa-methyldisilizane, Teflon, fluorocarbon, a polymer such as polyethylene glycol (PEG) and/or Parylene.

Embodiments of the present disclosure include a method for preparing a biological microarray. The steps of the method include forming wells on a substrate, wherein the wells are separated by metal interstitial regions; applying a polymer layer on the substrate such that the polymer layer covers the wells and the metal interstitial regions; cross-linking the polymer through the substrate; and removing the metal to yield a substrate and a plurality of polymer pads coupled to a surface of the substrate, wherein the polymer pads comprise a molecule binding substance. The metal interstitial regions can be configured as pillars in some embodiments. Alternatively or additionally the interstitial regions can form a flat surface into which the wells form depressions.

Embodiments of the present disclosure include a method for preparing a biological microarray. The steps of the method include forming an electrically conductive layer on a surface of a substrate; forming a plurality of spaced apart electrically nonconductive regions on the electrically conductive layer; forming a polymer layer over the electrically conductive layer and the plurality of spaced apart electrically nonconductive regions, wherein the polymer is coupled to a plurality of primers; and applying a current through the electrically conductive layer to deactivate only a portion of the primers coupled to the polymer.

Embodiments of the present disclosure include a method for preparing a biological microarray. The steps of the method include forming a polymer layer on a surface of a substrate; forming a plurality of spaced apart photoresist regions on the polymer; contacting exposed portions of the polymer layer with a plurality of primers; and removing the photoresist regions and covered portions of the polymer layer such that a plurality of spaced apart polymer pads coupled the plurality of primers remain on the surface of the substrate.

Embodiments of the present disclosure include a method for preparing a biological microarray. The steps of the method include forming wells on a substrate, wherein the wells are separated by photoresist interstitial regions; applying nanoparticles on the substrate such that the nanoparticles cover the wells and the photoresist interstitial regions; removing the photoresist such that a plurality of spaced apart nanoparticles remain on the surface of the substrate; and coupling a molecule binding substance to the nanoparticles. The photoresist interstitial regions can be configured as pillars in some embodiments. Alternatively or additionally the interstitial regions can form a flat surface into which the wells form depressions.

Embodiments of the present disclosure include a method for preparing a biological microarray. The steps of the method include (a) providing an amplification reagent comprising (i) an array of amplification sites, and (ii) a solution comprising a plurality of different target nucleic acids, wherein the different target nucleic acids have fluidic access to the plurality of amplification sites and wherein the solution comprises a molecular crowding agent such as a solution of at least 3% PEG. The method also includes reacting the amplification reagent to produce a plurality of amplification sites that each comprise a clonal population of amplicons from an individual target nucleic acid from the solution, wherein the reacting comprises (i) producing a first amplicon from an individual target nucleic acid that transports to each of the amplification sites, and (ii) producing subsequent amplicons from the individual target nucleic acid that transports to each of the amplification sites or from the first amplicon.

Embodiments of the present disclosure include a method for preparing a biological microarray. The steps of the method include (a) providing an amplification reagent in a flow cell comprising (i) an array of amplification sites, and (ii) a solution comprising a plurality of different target nucleic acids, wherein the different target nucleic acids have fluidic access to the plurality of amplification sites, and (b) applying an electric field across the flow cell to crowd the target nucleic acids towards the array of amplification sites (c) reacting the amplification reagent to produce a plurality of amplification sites that each comprise a clonal population of amplicons from an individual target nucleic acid from the solution, wherein the reacting comprises (i) producing a first amplicon from an individual target nucleic acid that transports to each of the amplification sites, and (ii) producing subsequent amplicons from the individual target nucleic acid that transports to each of the amplification sites or from the first amplicon.

Embodiments of the present disclosure include a biological microarray system that includes an array of base pads at predetermined sites on a substrate; a molecule binding substance disposed over each of the base pads; and a dendron coupled to each of the base pads, wherein the dendron comprises a plurality of ends and wherein the plurality of ends are functionalized with binding groups.

Embodiments of the present disclosure include a biological microarray system that includes an array of base pads at predetermined sites on a substrate; and at least one primer coupled to each of the base pads, wherein a first portion of the primers are coupled to the base pad at a first end and wherein a second portion of the primers are coupled to the base pads at a second end, wherein the first end comprises a cleavable portion.

Embodiments of the present disclosure include a biological microarray system that includes an array of base pads at predetermined sites on a substrate; a layer of silane-free acrylamide disposed on the substrate between the array of base pads, wherein the layer of silane-free acrylamide comprises a plurality of primers comprises a first adapter end and a second adapter end; and a second plurality of primers coupled to the base pads such that at least one primer is coupled to each of the base pads, wherein second plurality of primers comprises the first adapter end and a third adapter end.

Embodiments of the present techniques are described herein by reference to a microarray for use with a biological analysis device. The disclosure is not, however, limited by the advantages of the aforementioned embodiment. The present techniques may also be applied to devices capable of generating other types of biological data or for other types of molecule capture. Further, it should be understood that the disclosed embodiments may be combined with one another. In addition, features of particular embodiments may be exchanged with features of other embodiments.

DRAWINGS

These and other features, aspects, and advantages of the present invention will become better understood when the following detailed description is read with reference to the accompanying drawings in which like characters represent like parts throughout the drawings, wherein:

FIGS. 9-11 are diagrammatical representations of steps in the preparation of sites of the exemplary microarray once formed;

FIGS. 12 and 13 are diagrammatical representations of capture and amplification techniques for use with the exemplary microarray;

FIG. 14 is a diagrammatical representation of steps in the preparation of base pads in accordance with embodiments of the present techniques;

DETAILED DESCRIPTION

The present disclosure provides improved techniques for making and utilizing microarrays. The techniques may draw upon a range of different technologies for creating a prepared microarray ready to receive molecules of interest for analysis. The microarrays offered are particularly suited for capturing one or more molecules of interest at each site, and these molecules may be subsequently amplified to provide a generally uniform probe of the same molecule at the individual sites. The techniques may be used for microarray analysis and/or sequencing, such as sequencing of DNA and RNA (including cDNA. In certain embodiments, the techniques may be used with a variety of sequencing approaches or technologies, including techniques often referred to as sequencing-by-synthesis (SBS), sequencing-by-ligation, pyrosequencing and so forth.

Figure 1:
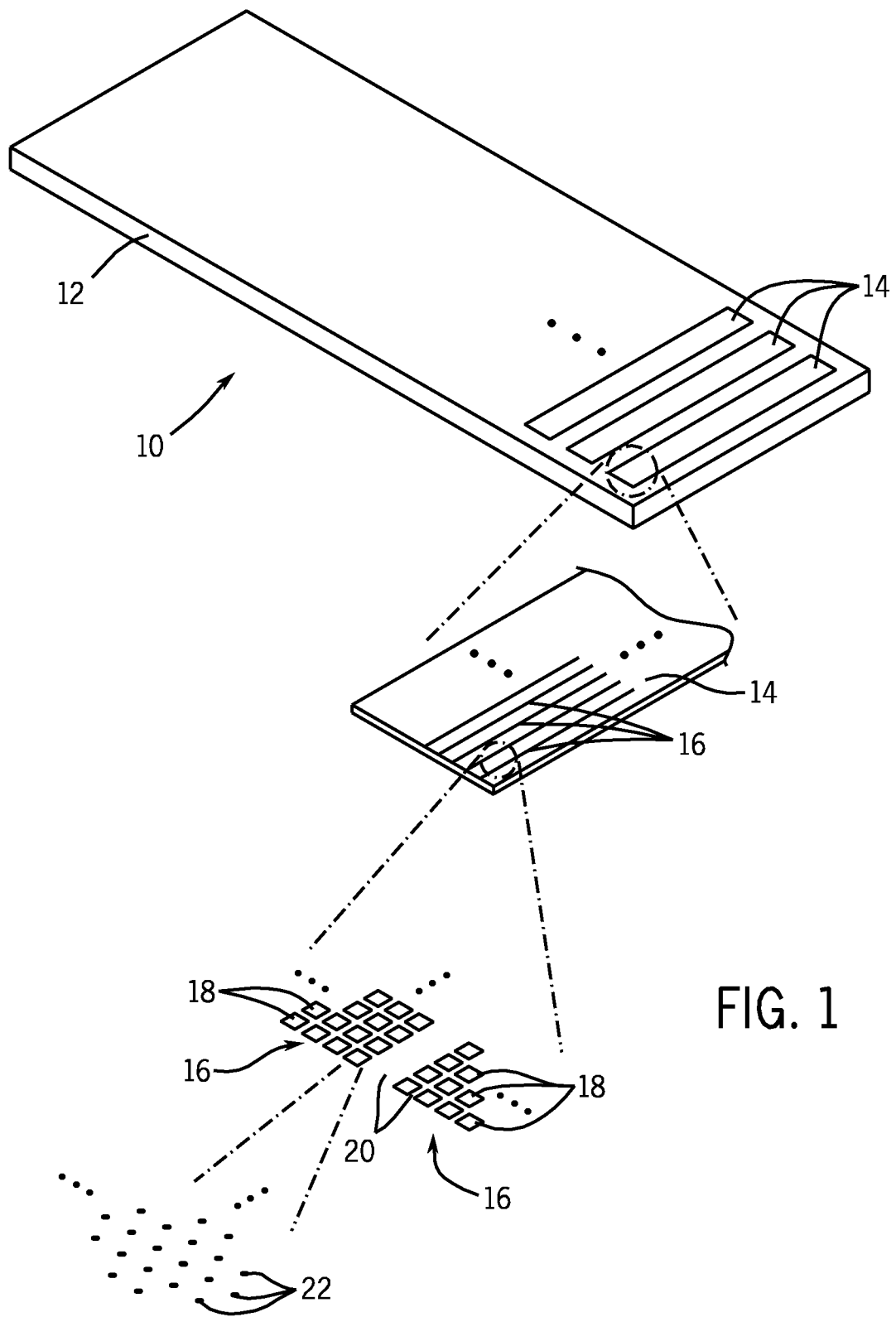
FIG. 1 is a diagrammatical representation of an exemplary microarray according to the present disclosure, illustrating the overall layout of the microarray and detailing the arrangement of individual sites.

Turning now to the drawings, and referring first to FIG. 1, an exemplary microarray 10 is illustrated for detecting and analyzing molecules of interest. In general, the microarray comprises a substrate 12 and sections 14 separated by open areas. The sections 14 may each comprise regions 16, which may generally form lines across the substrate. Each of these regions, in turn, comprises multiple domains 18, each separated from one another by open areas 20. Finally, the domains 18 comprise multiple individual sites 22 where the molecules of interest will be deposited and attached for analysis. As noted below, many different layouts of the sites may be envisaged, including regular, repeating, and non-regular patterns. In a presently contemplated embodiment, for example, the sites are disposed in a hexagonal grid for close packing and improved density. Other layouts may include, for example, rectilinear (i.e., rectangular) layouts, triangular layouts, and so forth. The particular layouts, and differences between the layouts of different domains, if used, may follow the teachings of U.S. Pat. No. 7,813,013, and/or of U.S. patent application Ser. No. 13/267,565, filed on Oct. 6, 2011 which are hereby incorporated by reference in its entirety. It should be noted that the patterned substrate (microarray) may also be used to control the density of the features capable of interrogation (e.g., through imaging). In addition to enabling a controlled increase in density, the present techniques also provide a means to control a lower density regime. It should also be noted that, as discussed below, the microarray illustrated and discussed in the present disclosure will typically be disposed in or formed as a part of a flow cell in which various carrier fluids, reagents, and so forth may be introduced. Moreover, the particular orientation of the features, sites, sections, domains and so forth may differ from those illustrated in FIG. 1. In some embodiments, the sections 14, regions 16, domains 18 and/or sites 22 are contiguous and thus need not be separated by open areas.

In many cases, the microarray will be used to analyze biological molecules, such as nucleotides, oligonucleotides, nucleic acids, amino acids, polypeptides, proteins, and other bioactive reagents at the sites, that may be prepared in advance. The resulting system may be designed for synthesizing one or more of the above biopolymers or sequencing such biopolymers. It should be borne in mind that the present techniques although useful for sequencing operations, gene expression operations, diagnostic applications, diagnostic applications, or any one of these, are not necessarily limited to those uses. For example the methods and compositions set forth herein may be used for manufacturing, preparing, imaging, and analyzing collected image data for any desired application The disclosed embodiments may be used with any known combinatorial chemistry or biochemistry assay process, and are especially adaptable to assays having solid phase immobilization. For example, the disclosed embodiments may be used in many areas such as drug discovery, functionalized substrates, biology, proteomics, combinatorial chemistry, and any assays or multiplexed experiments. Examples of common assays are SNP (single nucleotide polymorphism) detection, DNA/genomic sequence analysis, genotyping, gene expression assays, proteomics assay, peptide assays, antigen/antibody assays (immunoassay), ligand/receptor assays, DNA analysis/tracking/sorting/tagging, as well as tagging of molecules, biological particles, cell identification and sorting, matrix support materials, receptor binding assays, scintillation proximity assays, radioactive or non-radioactive proximity assays, and other assays, high throughput drug/genome screening, and/or massively parallel assay applications. The analyte of interest may be labeled, detected or identified with any technique capable of being used in an assay with arrays or beads, including but not limited to fluorescent, luminescent, phosphorescent, quantum dot, light scattering colloidal particles, radioactive isotopes, mass spectroscopy, NMR (nuclear magnetic resonance), EPR (electro paramagnetic resonance), ESR (electron spin resonance), IR (infrared), FTIR (Fourier transform infra red), Raman spectroscopy, or other magnetic, vibrational, electromagnetic, electrical, pH, chemical or optical labeling or detection techniques. Optical or non-optical detection techniques and optionally optical or non-optical labels can be used in a method or composition set forth herein. The invention provides array surfaces having the disclosed coatings and/or features.

In the illustrated embodiment, however, exemplary biological molecules might include, but are not limited to, any of a variety of molecules that have a biological activity or are reactive with biological systems. Examples include nucleic acids, such as DNA, RNA or analogs of DNA or RNA. Other exemplary biological molecules might include proteins (also referred to as polypeptides), polysaccharides or analogs thereof. Exemplary proteins include, but are not limited to, nucleic acid-specific proteins such as polymerases, transcription factors, single stranded binding proteins or restriction endonucleases; lectins; or avidin or analogs thereof. Other biological molecules include SNARE peptides, aptamers and ribosomes. The methods and compositions set forth herein need not be limited to analyzing biological molecules, being useful for example, with other types of biological materials such as cells or sub cellular particles such as organelles. Molecules and materials other than biological molecules and materials may be analyzed as well.

Although any of a variety of biopolymers may be used, for the sake of clarity, the systems and methods used for processing and imaging in the exemplary context illustrated in FIG. 1 and elsewhere herein will be described with regard to processing of nucleic acids. In general, the microarray of FIG. 1 comprises probes that may include one reaction site or an array of reaction sites. As used herein, the term "array" or "microarray" refers to a population of individual reaction sites on one or more substrates such that individual reaction sites may be differentiated from each other according to their relative location. Ideally, a single species of biopolymer may be attached to each individual reaction site, and the techniques described below facilitate such individualization. Moreover, multiple copies of particular species of biopolymer may be attached to a particular reaction site, such as by amplification of a single molecule or multiple molecules initially captured or seeded at the site. The array taken as a whole will typically include a plurality of different biopolymers, e.g., a plurality of clonal copies attached at a plurality of different sites. The reaction sites may be located at different addressable locations on the same substrate, and in many applications, such addressing, and indexing of the particular sites for subsequent data analysis, are carried on during the processing of the prepared microarray (e.g., imaging and image analysis).

In general, the microarrays made and used as set forth in the present disclosure will be intended, in many applications, for analyzing nucleic acids. As will be appreciated by those skilled in the art, such molecules will often be of interest in certain naturally occurring contexts, such as chromosomal and non-chromosomal DNA of living beings (humans, animals, plants, microbes, and so forth). However, as used herein, the term "nucleic acid" should be considered to include both naturally and non-naturally occurring variants.

Further, certain embodiments of the present disclosure relate to capture of a single molecule of interest per site on a microarray. This may be achieved by any suitable technique, such as via size exclusion. In addition, certain embodiments of the present disclosure may relate to the capture of multiple molecules of interest. For example, kinetic exclusion techniques may permit capture of multiple molecules of interest. Kinetic exclusion can exploit conditions that yield a relatively slow rate of target nucleic acid capture vs. a relatively rapid rate for making copies of the target nucleic acid. Alternatively or additionally, kinetic exclusion can exploit a relatively slow rate for making a first copy of a target nucleic acid vs. a relatively rapid rate for making subsequent copies of the target nucleic acid or of the first copy. In one embodiment, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site. Kinetic exclusion techniques such as those disclosed in U.S. Provisional Application No. 61/660,487, which is incorporated by reference in its entirety herein for all purposes, may be used in conjunction with the disclosed embodiments.

Figure 2:
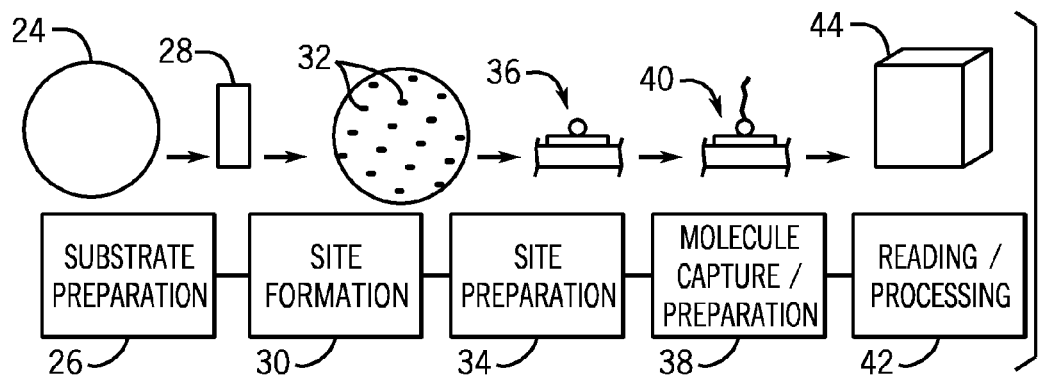
FIG. 2 is a diagrammatical representation of general phases in the manufacturing, preparation and use of such microarrays.

FIG. 2 generally represents certain phases included in the manufacture, preparation, and use of a microarray in accordance with the present disclosure. The microarrays may be formed from a blank 24 during a substrate preparation phase 26. The blank may be made of any suitable material, such as glass. Other suitable substrate materials may include polymeric materials, plastics, silicon, quartz (fused silica), borofloat glass, sapphire, plastic materials such as COCs and epoxies. The surface preparation phase 26 may include processes that predispose the blank 24 for efficient downstream processes such as site formation, site preparation, and molecule capture and preparation. The blank 24 is cut or sliced into substrate dies 28 which may generally have the form of the microarray. This initial substrate preparation phase is then followed by a site formation phase 30 in which the individual sites 32 are formed on the substrate. It should be noted that the operations may be performed in different orders and manners. For example, in a presently contemplated method, the array of capture sites are applied to a blank substrate prior to cutting the substrate from a wafer or blank that is used to form many microarrays. Functionalization of the capture sites, as described below, is performed after the cutting operation in this particular embodiment. A range of different techniques are presently contemplated for formation of the sites. One of these techniques is adapted to dispose a material at each site location that may be built upon for accommodating the molecule capture and amplification desired. Exemplary techniques include nano-imprint lithography, described in greater detail below, as well as dip pen lithography, photolithography, and micelle lithography. In one presently contemplated embodiment, the sites are formed by deposition of a base pad at each site location. The site pads may be made of any suitable material, such as gold or another metal. Other suitable material may include silanes, functional biomolecules such as avidin or functionalized organic or inorganic molecules, titanium, nickel, and copper. Alternatively, the site pads may be created by simply blocking the interstitial space with a resist or chemical moiety that resists attachment of a binding moiety leaving the site pad composed of native substrate material (i.e. glass, etc). The site pads can then be derivatized with binding moieties that react specifically with the substrate material (i.e. glass, etc.) and not interstitial space. It should be noted that the array of base pads could be an array of nanodots or nanoparticles. Further, the substrate may include any number and/or arrangement of image registration features.

Once the sites are laid out on the substrate, site preparation may proceed as indicated at reference numeral 34, resulting in a prepared microarray 36 ready to be further processed to receive a sample of molecules to be tested. This phase of the manufacturing process may include deposition of various materials on the pads, but also around the pads or over the entire extent of the substrate. These materials may be adapted to enhance the capture of one or more molecules at each site location, and optionally for subsequently amplifying the molecules for further reading analysis. In the exemplary embodiment, substrate preparation phase 26, the site formation phase 30, and the site preparation phase 34 may be thought of as the major steps in the manufacturing of the microarray. Thereafter, the microarray may be stored and utilized as described below. Moreover, any of the intermediate preparation stages may be performed by the same or separate entities, with intermediate products being further processed to arrive at the final prepared microarray. It should also be noted that while microarrays having a single prepared surface are illustrated and described here, as discussed below, the microarrays may be used in applications where more than one surface is prepared and used for molecule captures, amplification, reading and analysis. Moreover, the microarrays may typically be disposed in a flow cell that permits the introduction of chemistry useful for adding nucleotides and other substances, templates for reading, sequencing, and so forth, agents for deblocking locations on the templates, washing and flushing liquids, and so forth. Such flow cells are described, for example, in U.S. patent application publication no. US 2010/0111768 A1 and U.S. Ser. No. 13/273,666, each of which is hereby incorporated by reference in its entirety.

Once prepared for use, the microarray may be employed to capture one or more molecules at each site location as indicated by phase 38 in FIG. 2. The molecule or molecules will typically be amplified, such as by bridge amplification, although other amplification processes may also be used. For example, amplification of a template nucleic acid may be carried out using bridge amplification as described in Bentley et al., *Nature* 456:53-59 (2008); U.S. Pat. No. 5,641,658 or 7,115,400; or in U.S. Pat. Pub. Nos. 2002/0055100 A1, 2004/0096853 A1, 2004/0002090 A1, 2007/0128624 A1, or 2008/0009420 A1, each of which is incorporated herein by reference in its entirety. In this example, the bridge amplification may be primed by primer nucleic acids that are attached to a porous attachment layer that is in contact with a base pad to which a template nucleic acid is attached. Thus, the base pad can seed growth of a cluster of nucleic acid copies of the template that forms in the porous attachment layer around the base pad.

Another useful method for amplifying nucleic acids is rolling circle amplification (RCA). RCA may be carried out, for example, as described in Lizardi et al., *Nat. Genet.* 19:225-232 (1998) or US Pat. Pub. No. 2007/0099208 A1, each of which is incorporated herein by reference in its entirety. Also useful is multiple displacement amplification (MDA), for example, using a product of RCA (i.e. an RCA amplicon) as a template. Exemplary methods of MDA are described in U.S. Pat. Nos. 6,124,120; 5,871,921; or EP 0,868,530 B1, each of which is incorporated herein by reference in its entirety. In embodiments that include an amplification step, one or more primers that are used for amplification may be attached to a base pad or the porous attachment layer. The primers need not be attached to a base pad or a porous attachment layer in some embodiments.

A molecule that is captured at a site or otherwise used in a method or composition herein may be a nucleic acid that is single stranded or double stranded. Typically the nucleic acid will have a single copy of a target sequence of interest. Nucleic acids having concatameric copies of a particular sequence may be used (e.g. products of rolling circle amplification). However, in many embodiments the nucleic acid will not have concatameric copies of a sequence that is at least 100 nucleotides long or that is otherwise considered a target sequence for a particular application of the methods. Although the methods and compositions are exemplified with respect to capture of a nucleic acid molecule, it will be understood that other molecules and materials such as those set forth above in regard to microarray analysis can also be captured at a site or otherwise used.

The prepared microarray with the probes attached, as indicated by reference numeral 40, may then be used for analysis purposes. The reading/processing phase 42 is intended to include the imaging of the microarray, the use of the image data for analysis of the molecules captured and amplified at each of the sites, and so forth. More will be said about this reading/processing phase below. The entire processing system denoted generally by reference numeral 44 in FIG. 2, may include various imagers, readers, data analysis systems, and so forth as described generally in U.S. Pat. No. 7,329,860; U.S. patent application publication nos. US 2010/0111768 A1, or 2011/0220775 A1; or U.S. Ser. No. 61/438,486 or 13/006,206, each of which is hereby incorporated by reference in its entirety.

Figure 3:
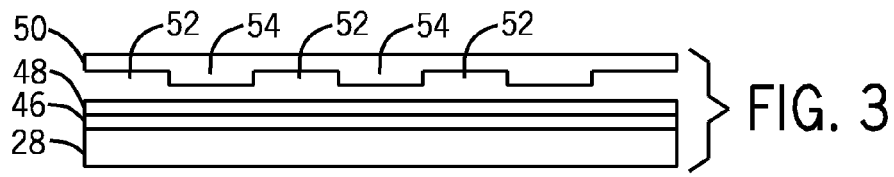
FIGS. 3-8 are diagrammatical representations of successive steps in the disposition of sites on a substrate for one of the microarrays.

As mentioned above, one presently contemplated approach for forming the base pads or site locations on substrate involves large-area patterning of very small features using techniques such as nanoscale imprint lithography. FIGS. 3-8 illustrate exemplary steps in an imprint lithography process. Referring first to FIG. 3, a substrate die 28 is first coated with a transfer layer 46, such as by spin or spray coating. This layer may be formed of a commercially available resist, such as chlorobenzene and a methylacrylate polymer, and may have a nominal thickness of approximately 70 nm. On this transfer layer, an ultraviolet (UV) imprint resist layer 48 is disposed. This layer also may be formed by a polymer which may be spin or spray coated on the transfer layer. This UV imprint resisted layer will form an etch barrier in subsequent processing. This layer may be formed, for example, of tert-butyl methylacrylate and polyester modified polydimethylsiloxane and polyester acrylate and a photo-initiator, at a nominal thickness of approximately 10 nm thicker than the feature height on the working mold 50, typically 70 nm. A working mold 50 is formed in advance, and may be made of various materials, such as glass or modified polydemethylsiloxane. The working mold will be generally transparent to UV light, to permit curing as described below. The desired pattern for the site pad will be formed in the working mold, such that recesses 52 will separate lands 54. The recesses 52 will generally correspond to spaces that will be formed around the pads on the substrate, while the lands 54 in this embodiment will generally correspond to the locations of the pads. The size of the separated lands may be tuned and can range, for example, from 5 nm (nanometers) to 3 μm (micrometers).

Figure 4:
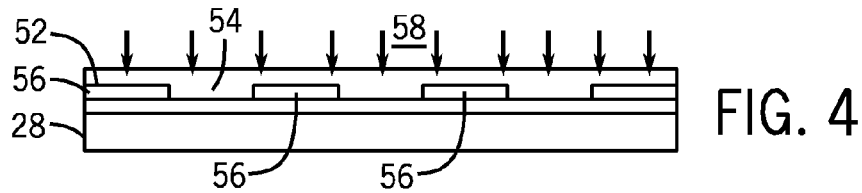
Figure 5:
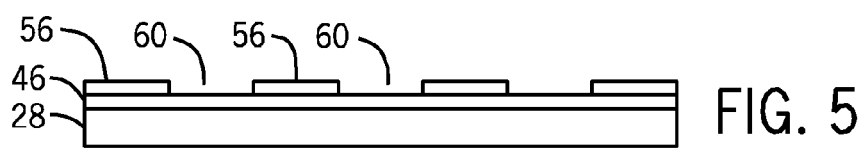
Figure 6:
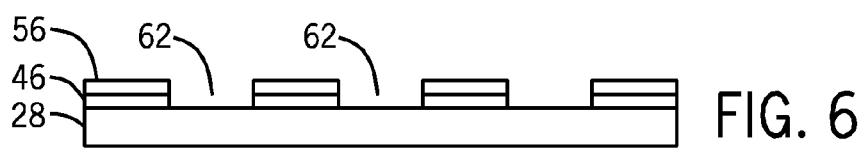
Figure 7:
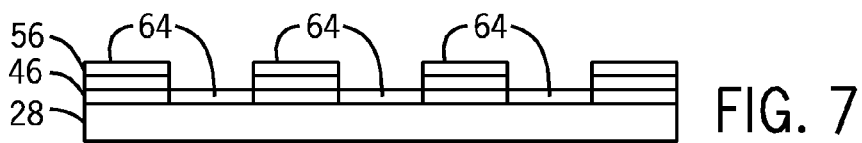
Figure 8:
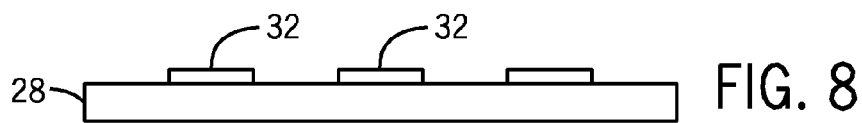

As illustrated in FIG. 4, during processing the mold is brought into contact with the UV imprint layer and displaces portions of this layer to form regions 56 within the recesses 52 of the mold. That is, the lands 54 displace the UV imprint resist layer such that the lands are generally adjacent to the underlying transfer layer. With the mold in place, then, the structure is exposed to UV radiation to at least partially cure the regions 56, rendering them resistant to subsequent etching and effectively transferring the pattern on the working mold into the resist. With the mold then removed, as illustrated in FIG. 5, the transfer layer 46 remains on the substrate die 28, and the remaining regions 56 of the UV imprint resist layer remain to protect the underlying regions of the transfer layer. Exposed transfer regions 60 remain at what will become the locations of the site pads. An etch process is then used to remove these regions as illustrated in FIG. 6. Once the exposed transfer regions are removed, exposed substrate regions 62 will remain. Subsequently, the structure is subjected to a deposition process, such as a metal deposition, to deposit a layer of material 64 over both the regions 56 and the exposed substrate regions 62. In a currently contemplated embodiment, the deposition is of a thin layer of gold, although other materials may include Al, $Al_2O_3$, Zn, ZnO, Ni, Ti, $TiO_2$, ITO (Indium tin oxide), etc. Moreover, the deposition may be to any desired thickness, such as a nominal thickness of 5 nm. Finally, in a lift-off step, the layers above and below the regions 56, including these regions themselves are removed to leave only the pads at locations 32 and the substrate. This lift-off operation may involve solvent washing steps and sonification. Following these processes, a substrate die will be provided with the sites determined and formed in the desired pattern of sites, domains, regions, and so forth.

Once the sites are laid out and formed by positioning the site pads on the substrate, subsequent building of the sites and preparation steps may take place. As illustrated in FIG. 9, in a presently contemplated embodiment, each base pad 68 receives a capture substance 70 designed to promote the capture of a molecule of interest. FIG. 9, as with other figures in this disclosure, is not necessarily drawn to scale. For example, the capture substance may be submicroscopic in size (e.g. a linker molecule) or may be a particle that is, at least in some cases, visible under a microscope. In a presently contemplated embodiment, the substance comprises thiol-avidin, although other substances may be utilized, such as silanes, biotin-binding proteins, functional biomolecules such as avidin, streptavidin, neutravidin, and functionalized organic or inorganic molecules. An example is a gold-patterned array functionalized with thiol-avidin to bind molecules modified with biotin. Other capture substances may include, for example, biological binding molecules including neutravidin, streptavidin, antibodies, etc., chemical binding moieties such as amines, aldehydes, carboxyl groups, etc.; and inorganic binding moieties such as metal chelates (i.e. histidine binding), gold (thiol binding), etc.

A capture substance may be attached to a base pad or site via a covalent or non-covalent linkage. Exemplary covalent linkages include, for example, those that result from the use of click chemistry techniques. Exemplary non-covalent linkages include, but are not limited to, non-specific interactions (e.g. hydrogen bonding, ionic bonding, van der Waals interactions etc.) or specific interactions (e.g. affinity interactions, receptor-ligand interactions, antibody-epitope interactions, avidin-biotin interactions, streptavidin-biotin interactions, lectin-carbohydrate interactions, etc.). Exemplary linkages are set forth in U.S. Pat. Nos. 6,737,236; 7,259,258; 7,375, 234 and 7,427,678; and US Pat. Pub. No. 2011/0059865 A1, each of which is incorporated herein by reference.

As illustrated in FIG. 10, then, in a presently contemplated embodiment a charged layer 72 may be disposed over the pads and capture substance. In this embodiment, if used, the charged layer comprises aminopropyltriethoxysilane (APTES). This charged layer may promote the attachment of the molecules at each site, while preventing attachment where not desired. As illustrated in FIG. 11, an attachment layer 74 is disposed over at least the pads 68, and in the illustrated embodiment may be disposed over the entire substrate. In other embodiments, the attachment layer may be patterned such that it is present over the pads or sites but substantially absent over interstitial regions between the pads or sites.

An attachment layer used in a method or composition herein may be formed of a micro-porous material, such as silane-free acrylamide (SFA). Silane-free acrylamide (SFA) polymer may be formed by polymerization of silane free acrylamide and N-(S bromoacetamidylpentyl) acrylamide (BRAPA). Other attachment layers that may be used include without limitation, acrylamide, methacrylamide, hydroxyethyl methacrylate, N-vinyl pyrrolidinone or derivatives thereof. Such materials are useful for preparing hydrogels. In some embodiments, the polymerizable material can include two or more different species of compound that form a co-polymer. Exemplary hydrogels and polymerizable materials that may be used to form hydrogels are described, for example, in US Pat. Pub. No. 2011/0059865 A1, which is incorporated herein by reference in its entirety. Other hydrogels include but are not limited to, polyacrylamide polymers formed from acrylamide and an acrylic acid or an acrylic acid containing a vinyl group as described, for example, in WO 00/31148 (incorporated herein by reference in its entirety); polyacrylamide polymers formed from monomers that form [2+2] photo-cycloaddition reactions, for example, as described in WO 01/01143 or WO 03/014392 (each of which is incorporated herein by reference in its entirety); or polyacrylamide copolymers described in U.S. Pat. No. 6,465,178, WO 01/62982 or WO 00/53812 (each of which is incorporated herein by reference in its entirety). PAZAM is also useful as set forth in further detail below. The attachment layer can function to attach the molecules and/or it can provide locations for attachment of identical molecules (i.e. copies of the molecules) at each site during amplification.

As noted above, various layouts may be envisaged for the sites of the microarray. Moreover, the density, location, pitch, and sizes of the sites may vary depending upon such factors as the array design, the type of processing and imaging equipment used for analyzing the arrays, and the molecules to be processed. By way of example, presently contemplated sites made as set forth in the present disclosure may have sizes dictated by the desired imaging and/or reaction modality. For example, sites may be approximately 30-500 nm and may be in a range of 30-300 nm or 300-500 nm. The sites may be disposed on the substrate in a hexagonal pattern. The sites may be present at a density of approximately 1 million capture sites per square millimeter, but can easily be tuned by adjusting the pitch to densities greater than 5 million capture sites per square millimeter. While the particular pitch of the sites may vary, depending, for example, upon their size and the density desired, typical pitches may include at most about 5 micron, 2 micron 1 micron, 850 nm, or 750 nm, or even lower value.

The sites or pads used in various embodiments may be in a size range that is useful for capture of a single nucleic acid template molecule to seed subsequent formation of a homogenous colony, for example, via bridge amplification. FIG. 12 illustrates a base pad 68 that is attached to a capture substance 70 that is in turn attached to a single nucleic acid template 76. The nucleic acid template is illustrated as extending out of the attachment layer 74. However, in some embodiments the nucleic acid template may be retained under or within the volume of the attachment layer. Bridge amplification may be primed by primer nucleic acids that are attached to the attachment layer (e.g. the attachment layer may be a gel) to seed growth of a cluster of nucleic acid copies of the template that forms in or on the attachment layer around the base pad 68.

In an exemplary bridge amplification method, a template nucleic acid hybridizes to a gel-attached primer and the 3' end of the primer is extended to create a complementary copy of the template. In some embodiments two different primers may be attached to the gel. The primers can form a pair used for amplification of a template and its complementary copy. As such, two primers may be used for amplification of the template into multiple copies to form a nucleic acid cluster or population of amplicons. For example, amplification may be carried out using bridge amplification to form nucleic acid clusters attached to the gel. Useful bridge amplification methods are described, for example, in U.S. Pat. Nos. 5,641,658 and 7,115,400; U.S. Pat. Pub. Nos. 2002/0055100 A1, 2004/0096853 A1, 2004/0002090 A1, 2007/0128624 A1, and 2008/0009420 A1, each of which is incorporated herein by reference in its entirety. Any of a variety of solid phase amplification techniques can be used such as solid phase PCR (whether isothermal or thermocyclic) using a first primer species that is solid phase attached and a second primer species that is in solution. Other useful methods for amplifying nucleic acids using one or more gel-attached primers are rolling circle amplification (RCA) and multiple displacement amplification (MDA).

In particular embodiments, a cluster of nucleic acids may have a foot print that is no larger than the area of the base pad. For example, the attachment layer 74 may be confined to the foot print of the base pad 68. As such the base pad (and optionally the attachment layer) can form a cluster restriction zone along the lines illustrated in FIG. 13. Alternatively, the foot print of a cluster may be larger than the base pad 68 from which it was seeded.

One aspect of the present techniques disclosed herein relates to a process for preparing a polymer coating immobilized to a surface of a substrate. In some embodiments, the method comprises polymerizing a polymerizable material, which may be any suitable polymer in accordance with the present techniques, on a surface 90 of a substrate (e.g., substrate die 28), wherein the surface comprises a plurality of functional groups, thereby forming a layer of polymer coating over all or a part of the surface. The polymer coating can be covalently bonded to the functional or reactive groups on the surface. In certain embodiments, the microarrays may also use base pads 68 formed via selective patterning as illustrated in FIG. 14, which represents stages included in one example of the manufacture and preparation of a microarray including base pads 68 in accordance with the present disclosure. Further, the disclosed techniques for surface patterning may be used with other suitable site materials to form base pads, either with or without polymers.

As illustrated in FIG. 14, the substrate die 28 is coated with a polymer layer 100 (e.g., via spin coating or dunk coating) with one or more photoresist layers 102 disposed over the polymer layer 100 such that the polymer layer 100 is between the die 28 and the photoresist layer(s) 102 at stage 104. After a photolithography step 106, the surface 90 of the substrate die 28 includes an intact polymer layer 100 and wells 108 in the photoresist layer 102 after removal of a portion of the photoresist layer 102 to expose portions 110 of the polymer layer 100 that will be removed in subsequent steps. After an etching step 114 (e.g., reactive ion etching), portions 110 of the polymer layer 100 have been removed to expose the surface 90 of the substrate die 28. After a liftoff step 116, the base pads 68 are in place on the surface 90 of the substrate die 28 following liftoff of the remaining photoresist layer 102. The preparation of the base pads 68 may include one or more of lithography, imprint lithography, and etching steps. Further primer grafting can be performed at the beginning, during or at the end of the proposed sequence, before photoresist deposition or can follow the exposure of the base pads 68 as a solution-based technique.

Figure 15:
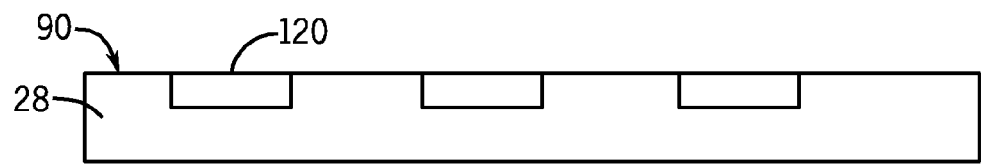
FIG. 15 is a diagrammatical representation of reactive pads formed in a substrate in accordance with embodiments of the present techniques.

FIG. 15 is an example of an alternate technique for forming base pads 68. In the depicted embodiment, the substrate die 28 is functionalized to form chemically reactive pads 120 on the surface 90 having the desired pattern. For example, if the substrate die 28 is glass, the reactive pads may be reactive silane pads. The polymer formation is limited to only the reactive portions of the substrate die 28. The substrate die 28 may be formed first, and the reactive pads 120 may be functionalized by any suitable patterning technique, such as the photolithography, etching, and or masking techniques provided herein.

Figure 16:
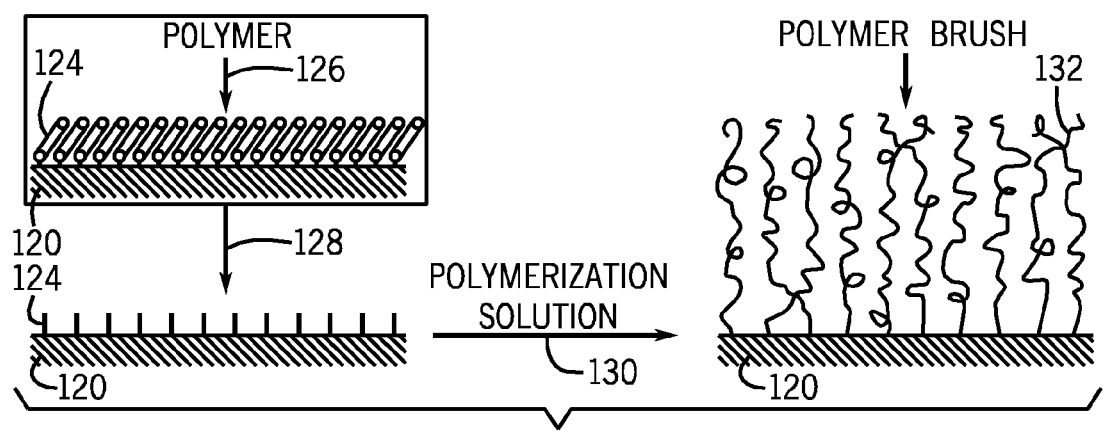
FIG. 16 is a diagrammatical representation of steps in the preparation of a polymer layer in accordance with embodiments of the present techniques.

FIG. 16 is a schematic depiction of the formation of a polymer brush polymer on a reactive pad 120. A self-assembling monomer layer 124 is contacted with the reactive pad 120 at step 126. The monomers form covalent bonds with the reactive pads 120 at step 128 and then are polymerized at step 130 to form a polymer brush 132. The polymer pads are then directly grown from the chemically reactive pads 120. In the depicted example, primer grafting may be done before, during or after polymerization is complete and may be a homogenous or heterogeneous reaction.

In one or more of the embodiments set forth herein, the polymer may be a poly(N-(5-azidoacetamidylpentyl)acrylamide-co-acrylamide) (PAZAM) polymer. For example, such polymers may be those disclosed in U.S. Provisional Application No. 61/657,508. In one specific embodiment, the polymer comprises a polymer of Formula (I)

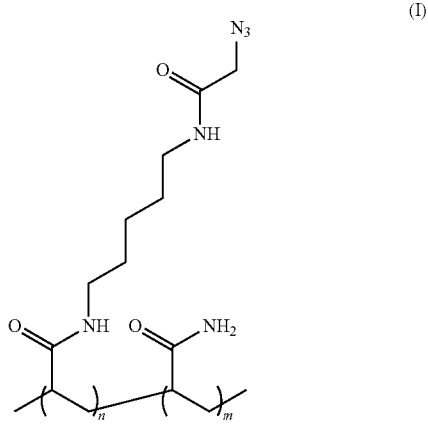

where n is an integer in the range of 1-10,000, and m is an integer in the range of 1-10,000. Further, in one embodiment, the molecular weight of the polymer may be about 300 kDa to 500 kD, or, in a specific embodiment, about 312 kDa. In embodiments in which a PAZAM polymer is implemented, polymerization may take place via a surface initiated atom transfer radical polymerization (SI-ATRP) (as shown in FIG.

Figure 17:
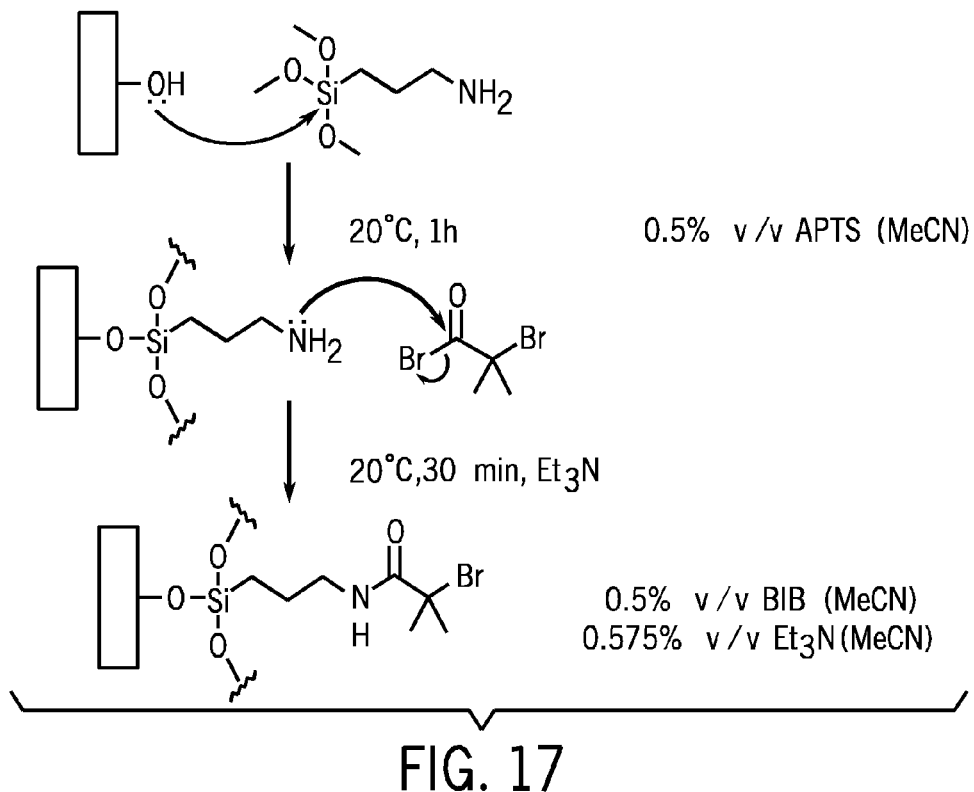
FIG. 17 is a diagrammatical representation of steps in the preparation of a polymer layer in accordance with embodiments of the present techniques.

17) to a silanized surface. As shown in FIG. 17, the surface is pre-treated with APTS (methoxy or ethyoxy silane) to covalently link silicon to one or more oxygen atoms on the surface (without intending to be held by mechanism, each silicon may bond to one, two or three oxygen atoms as indicated by the generic bonding structure in FIG. 17). This chemically treated surface is baked to form an amine group monolayer. The amine groups are then reacted with Sulfo-HSAB to form an azido derivative. UV activation at 21 degrees C. with 1 to 30 J/cm$^2$ of energy generates the active nitrene species, which can readily undergo a variety of insertion reactions with the PAZAM. In the depicted embodiment, the polymer may include a Br precursor to the azide chain that acts as a cross-linker.

Figure 18:
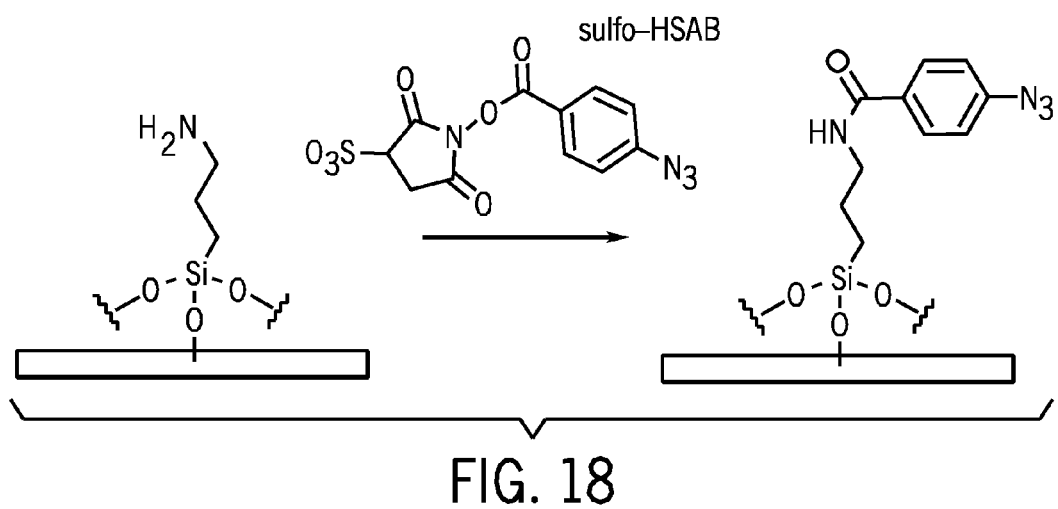
FIG. 18 is a diagrammatical representation of steps in the preparation of a polymer layer in accordance with embodiments of the present techniques.
Figure 19:
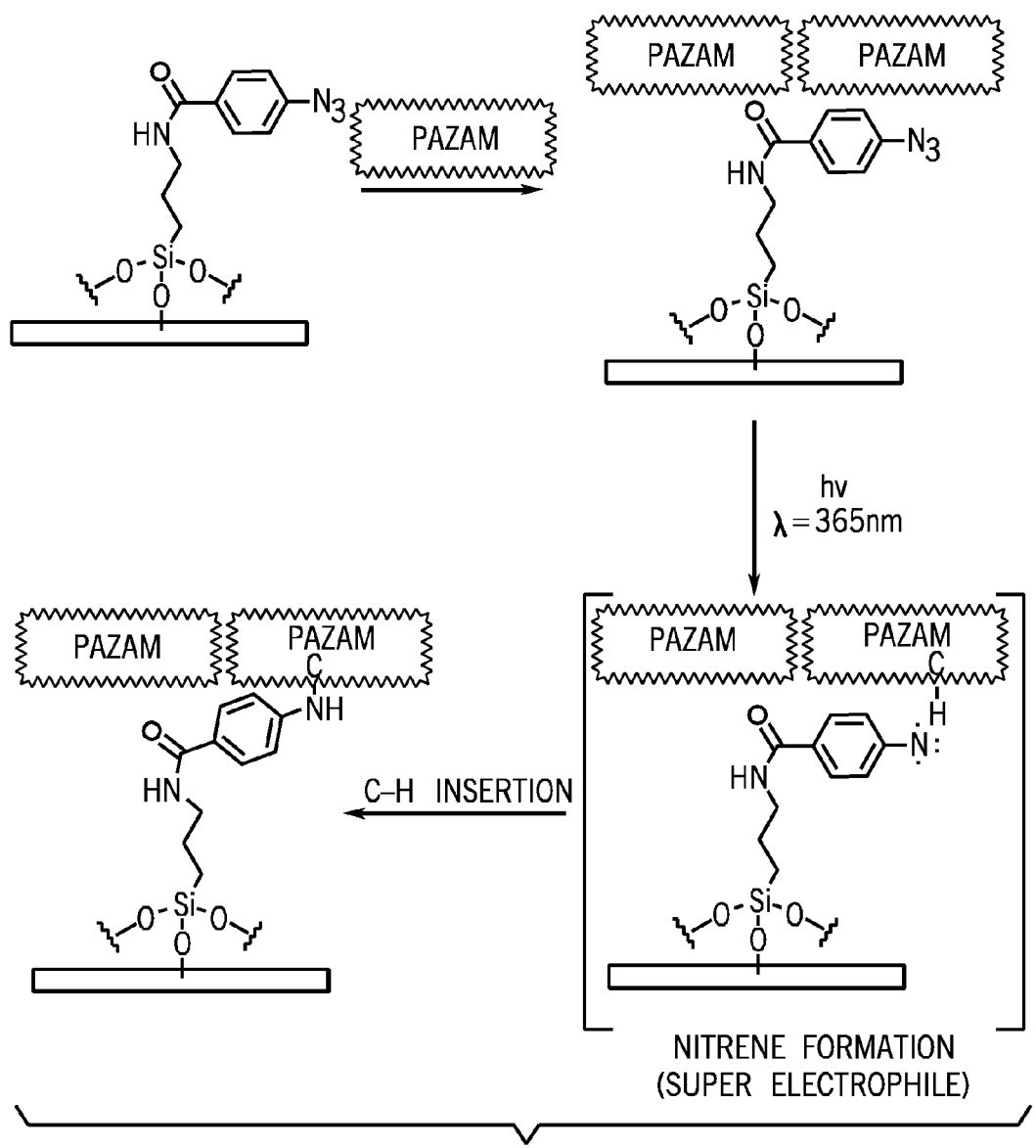
FIG. 19 is a diagrammatical representation of steps in the preparation of a polymer layer in accordance with embodiments of the present techniques.

FIG. 18 is a reaction diagram of UV-mediated linking of PAZAM monomers to an amine-functionalized surface, such as those generated via SI-ATRP reactions. The reaction begins with linking a photoactive coupling agent N-hydroxysulfosuccinimidyl-4-azidobenzoate (sulfo-HSAB). Sulfo-HSAB is a commercially available bifunctional crosslinking agent including a photoactive aryl azide and an activated NHS unit. Upon exposure to UV light (250-374 nm), the aryl azide generates a nitrene with the release of nitrogen. This highly reactive species can undergo a variety of rapid insertion reactions. As illustrated in FIG. 19, after the photoactive unit is attached, the PAZAM is deposited (e.g., via open wafer or flowthrough), followed by UV irradiation and linking.

Figure 20:
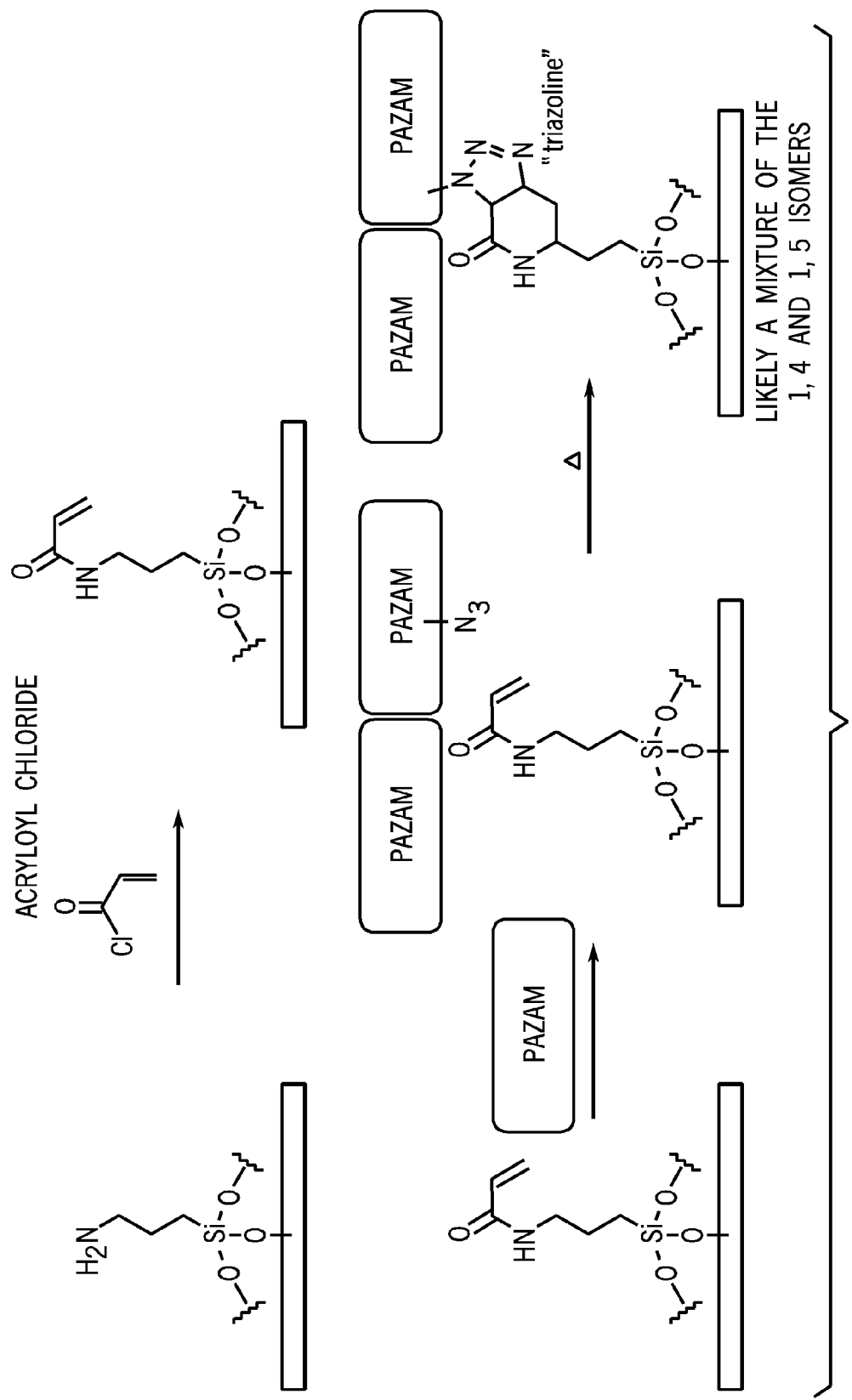
FIG. 20 is a diagrammatical representation of steps in the preparation of a polymer layer in accordance with embodiments of the present techniques.

FIG. 20 is an alternative thermal linkage reaction for linking PAZAM to the substrate die 28 (e.g., via chemically reactive pads 120). In the depicted embodiment, the reaction begins by thermally linking the active group (acryloyl chloride or other alkene or alkyne-containing molecule) with subsequent deposition of PAZAM and application of heat. It is contemplated that the thermal linkage reaction may yield a mixture of the 1,4 and 1,5 isomers and also adducts resulting from the 1,4 addition to the conjugated alkene moiety.

Figure 21:
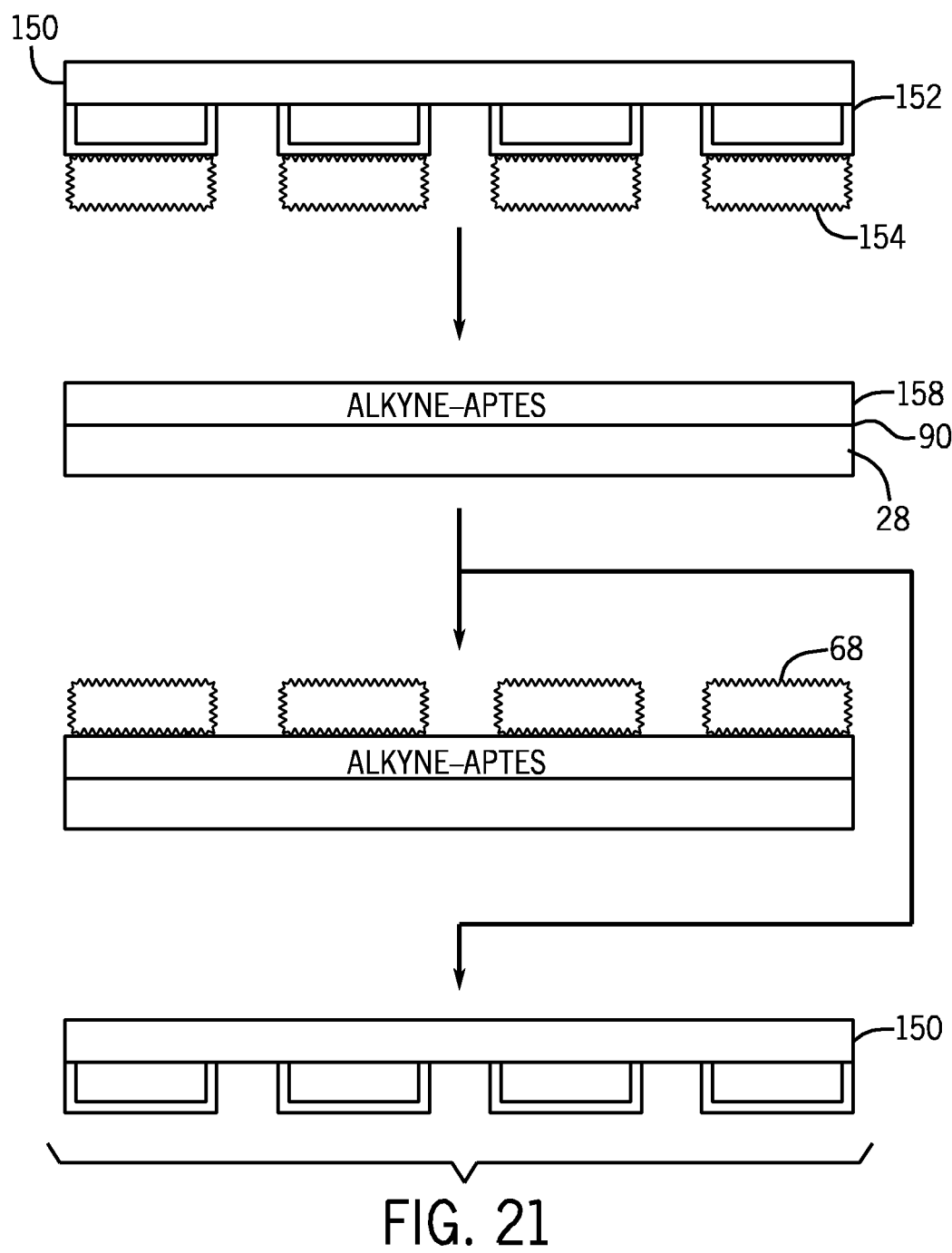
FIG. 21 is a diagrammatical representation of steps in the preparation of base pads in accordance with embodiments of the present techniques.

In addition to approaches in which a polymer layer is applied directly to the substrate die surface by growing the polymer layer in place, a microcontact printing approach is also contemplated. This approach, shown in FIG. 21, uses a soft or hard stamp 150 that has pillars 152 coated with a patterning medium 154. The medium may include polymers (including PAZAM), reactants, binders, surfactants, and/or catalysts. The stamp selectively delivers the patterning medium to defined regions on the substrate die 28. As shown, the surface 90 of the substrate die 28 may include an alkyne-APTES layer 158 or suitable reactive medium onto which the base pads 68 (or other types of base pads) are applied. The result is a patterned substrate die 28 including base pads, such as base pads 68 that support DNA cluster formation sequencing. In the depicted embodiment, primers may be grafted before, during or after patterning, could be present in the patterning medium, and could be grafted via homogenous or heterogeneous reactions.

It is contemplated that the base pads 68 (including, but not limited to, PAZAM polymers) are coupled to the substrate die 28 via covalent or non-covalent attachment protocols. In any of the disclosed embodiments, a photoresist material may protect the interstitial regions of the substrate die 28 from reacting/absorbing the polymer that is applied during formation of the base pads 68. A liftoff of the photoresist protective layer leaves behind only surface-attached polymer. Primer grafting to the base pads 68 for subsequent molecule capture may follow via homogeneous or heterogeneous methods.

Figure 22:
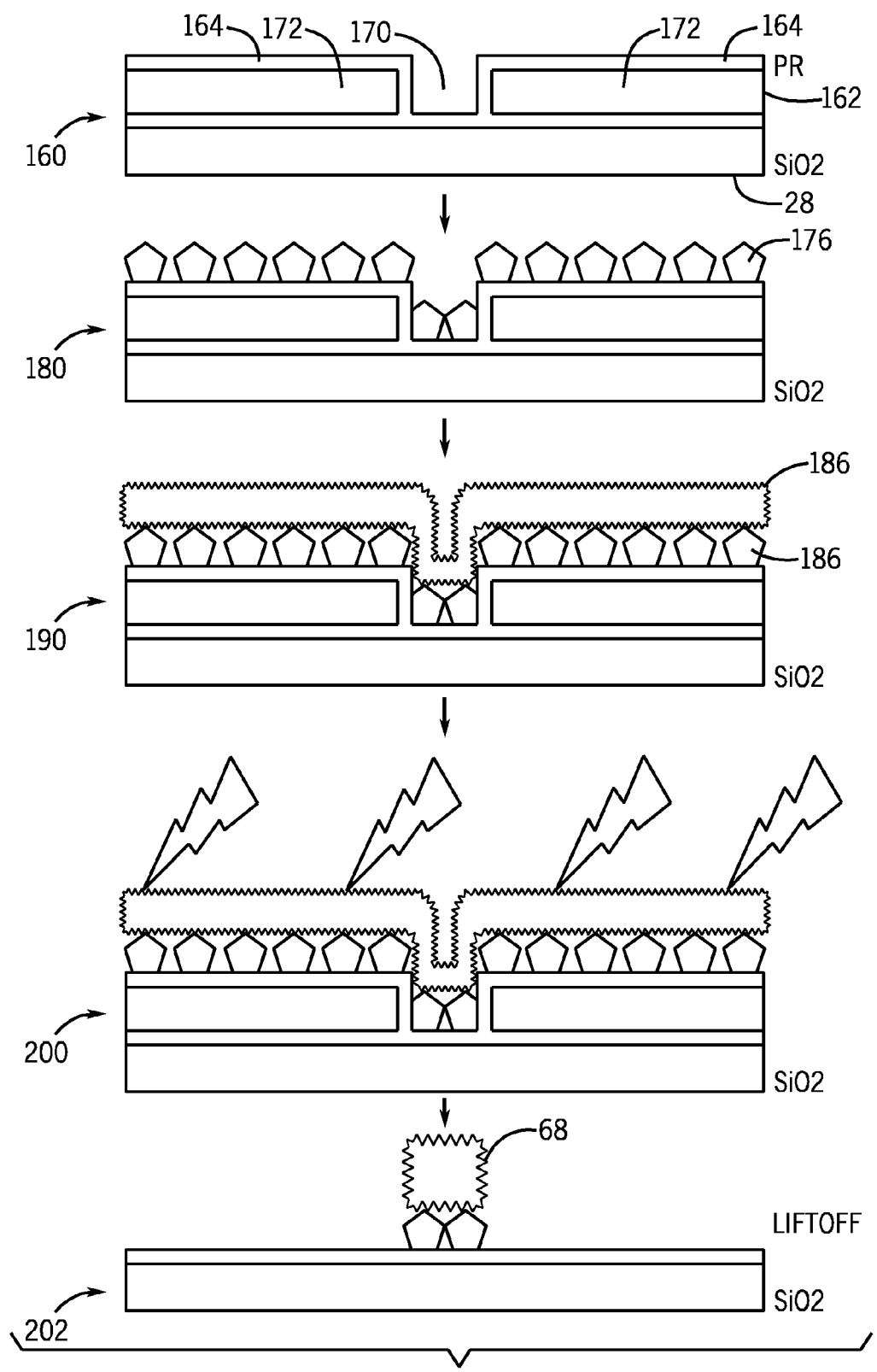
FIG. 22 is a diagrammatical representation of steps in the preparation of base pads in accordance with embodiments of the present techniques.

FIG. 22 illustrates various stages in one embodiment of a PAZAM base pad 68 attachment technique using a sulfo-HSAB photoactive coupler. At stage 160, the photoresist layer 162 is deposited on a reactive surface 164 of the substrate die 28. The photoresist layer 162, as depicted, forms reactive wells 170 and interstitial regions 172 that are elevated relative to the wells (e.g. forming pillars). After application of the coupling agent 176 (stage 180), which covers the wells 170 and the interstitial regions 172, a PAZAM layer 186 is deposited and/or formed on the coupling agent 176 (stage 190). As depicted, the PAZAM layer 186 fills in the wells 170 and covers the interstitial regions 172. Thus PAZAM can conform to surface contours having appropriately sized features. For example, wells having an opening with a cross section that is greater than about 100 $nm^2$ can be filled with PAZAM. It is contemplated that wells having smaller cross sections can be used as well under conditions where PAZAM fills the well or alternatively covers the well without entering the space of the well. After application of light (stage 200) to facilitate linking of the PAZAM layer 186, the photoresist layer 162 is lifted off (stage 202), leaving only attached PAZAM base pads 68. In the depicted embodiment, excess PAZAM in the wells 170 that is unlinked is also lifted off with the photoresist.

Figure 23:
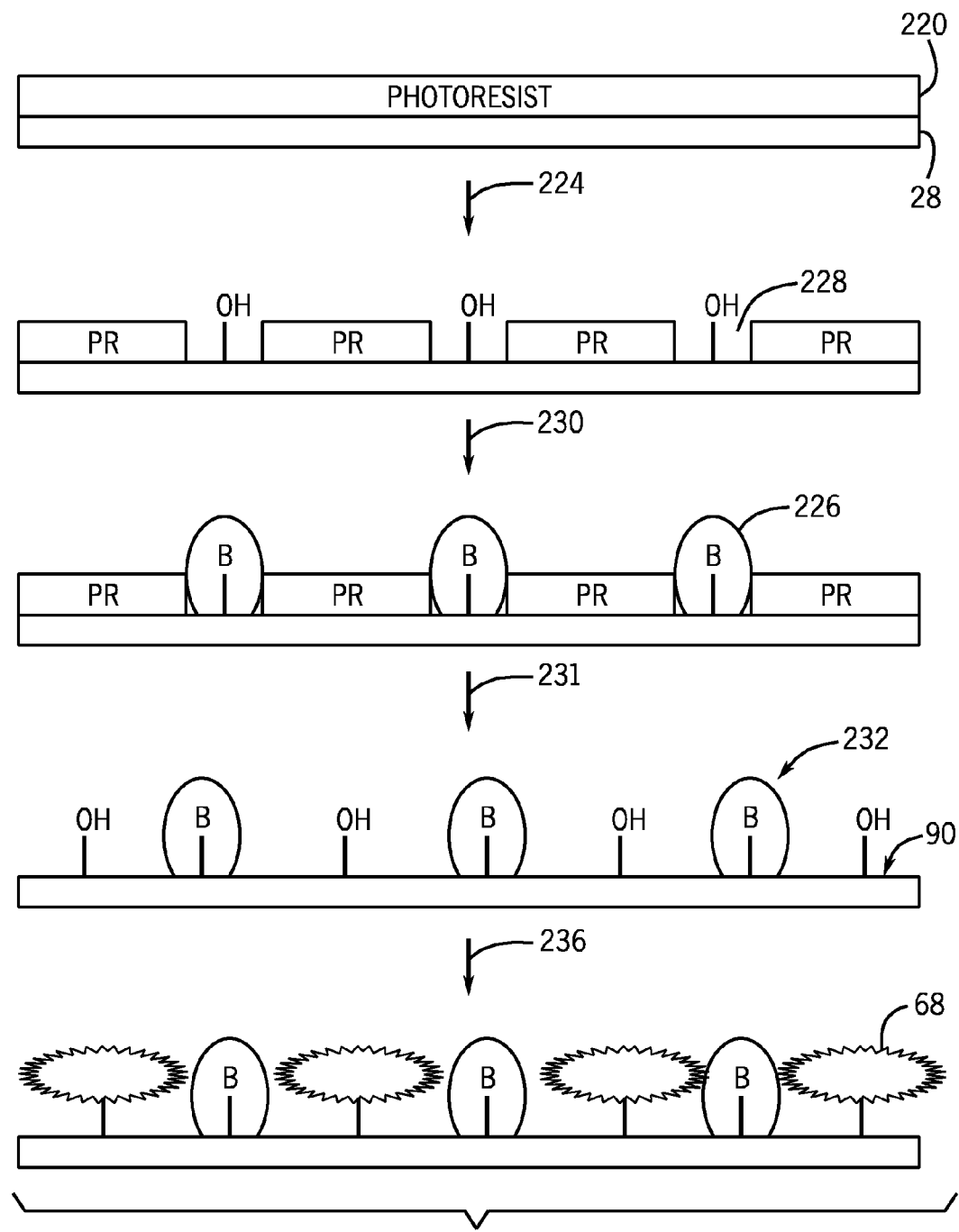
FIG. 23 is a diagrammatical representation of steps in the preparation of base pads in accordance with embodiments of the present techniques.

In certain embodiments, passivating the interstitials between the pads 68 may prevent nonspecific binding during capturing, sequencing or other applications. That is, in addition to forming a desired pattern of active base pads 68, the interstitial spaces may be treated to discourage undesired molecule binding. FIG. 23 illustrates an example in which lithography, or another patterning method, is employed to block sections of the surface 90 of the substrate die 28 to create inert pads. As illustrated, after patterning a photoresist layer 220 via lithography (step 224), a passivation material 226 is applied at step 230 to the interstitial spaces 228 exposed after patterning. Such passivation materials may include, but are not limited to, diamond-like carbon, polyethylene glycol, hexa-methyldisilizane, Teflon, and/or Parylene. The application of the passivation material 226 and subsequent liftoff (step 231) of the remaining photoresist later 220 yields a patterned surface with inert pads 232 forming the negative space of the desired pattern. The base pads 68 of any desired polymer may then be applied (step 236) to the surface 90 of the substrate die 28

Figure 24:
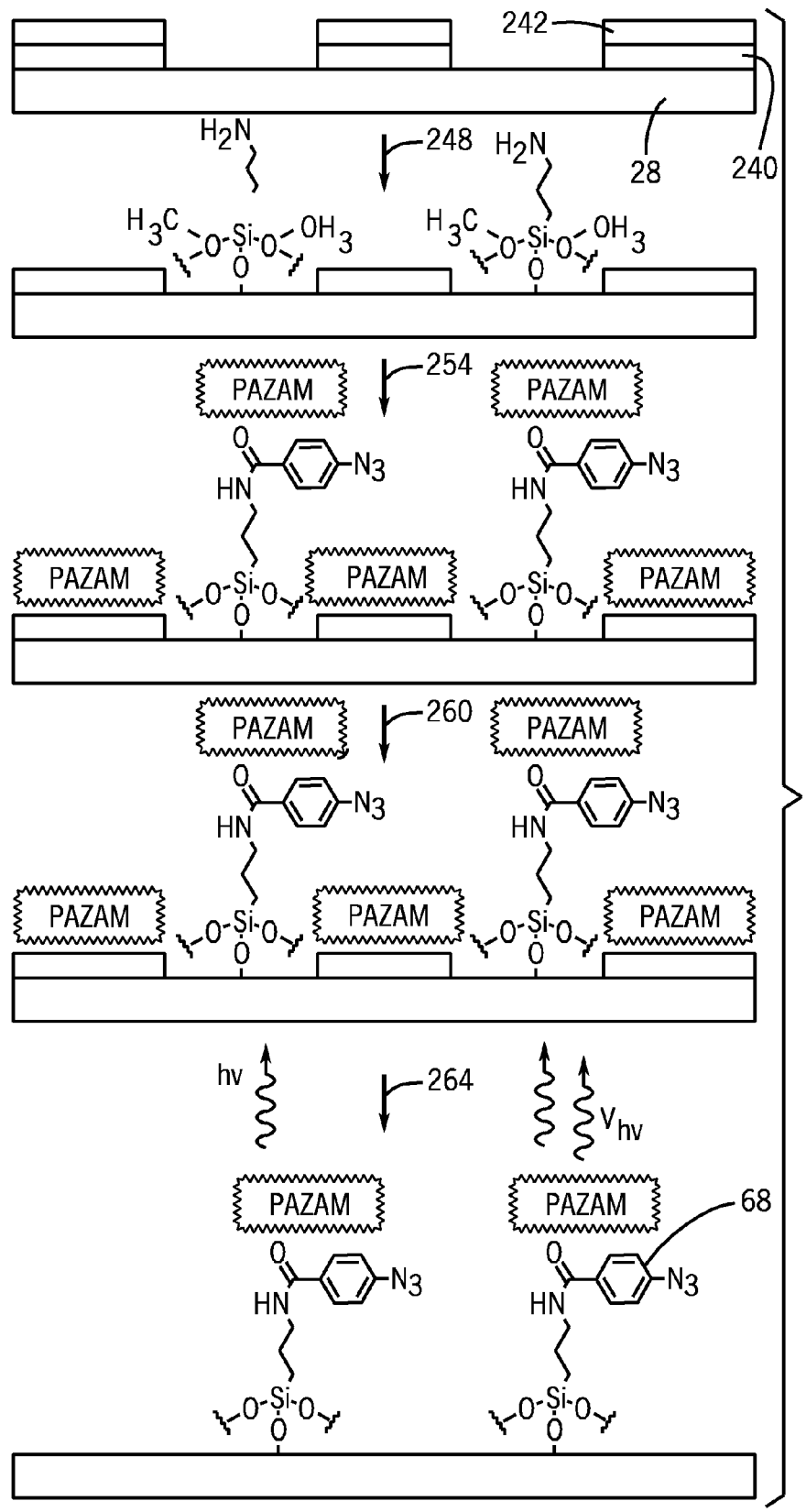
FIG. 24 is a diagrammatical representation of steps in the preparation of base pads in accordance with embodiments of the present techniques.

In an alternative approach, the surface 220 of the substrate die 28 may be passivated via metal patterning. In the approach illustrated in FIG. 24, a metal patterning sublayer 240 protects the interstitial during deposition. The metal patterning sublayer may be formed from one or more of aluminum, gold, titanium, as well as other metals. Metal can act as a photo- and chemical mask during the surface linkage step, and the liftoff of the metal is a chemically simple procedure, which may eliminate manufacturing steps relative to other processes. The metal layer 240 may include a photoresist layer 242 on an outermost surface. After APTMS and resist liftoff at step 248, the surface is ready for application of, for example, a PAZAM spin coat at step 254. The PAZAM layer is cross-linked, for example via backside illumination through the die 28, at step 260, and the base pads 68 (PAZAM pads in the depicted embodiment) are exposed after metal liftoff at step 264.

Figure 25:
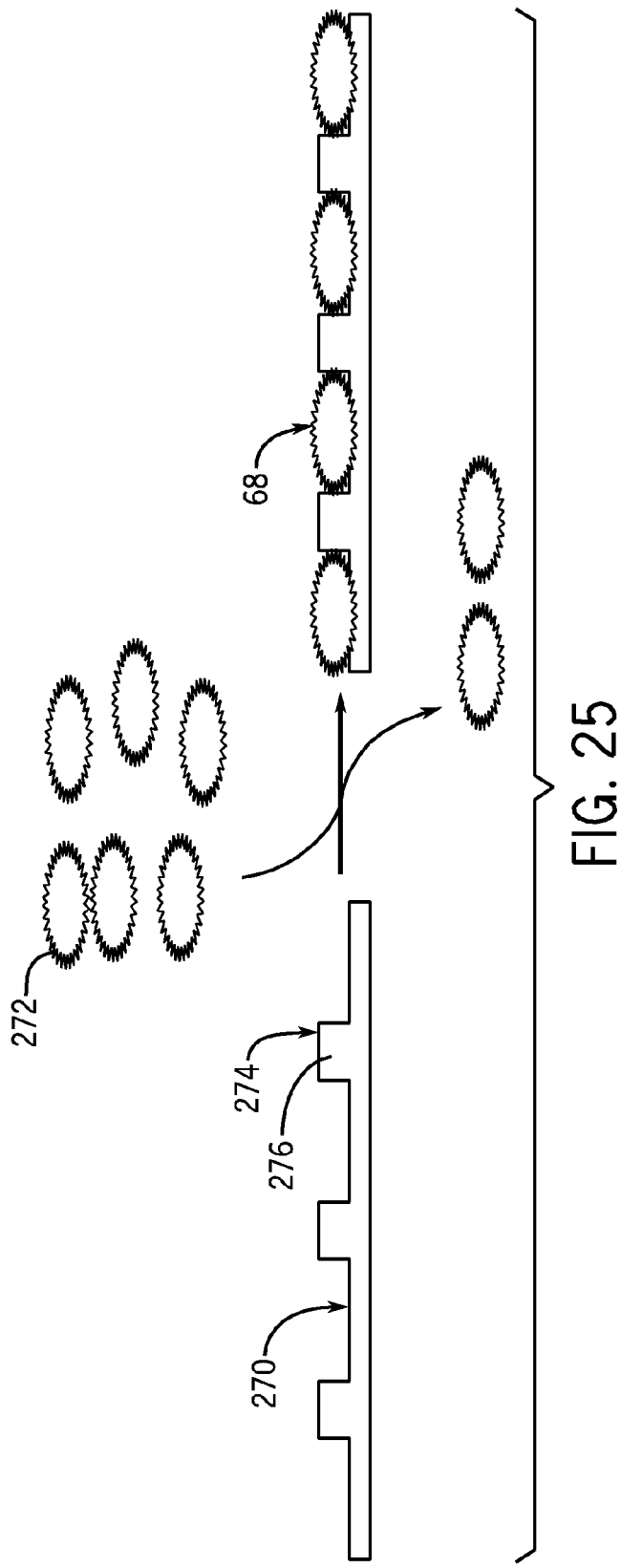
FIG. 25 is a diagrammatical representation of steps in the preparation of base pads and wells in accordance with embodiments of the present techniques.

FIG. 25 is an example of selectively functionalized wells 270 used for applying a polymer 272 only in the wells. For example, wells 270 may be functionalized with covalent linkage methods or the polymer may be noncovalently lodged in the surface. The fabrication of wells 270 offers a simpler approach to surface functionalization. In one embodiment, a passivation layer may be applied only to the tops 274 of the interstitial regions 276 to keep the top surface clean if necessary. Pregrafted or ungrafted PAZAM, or other polymer, may be applied.

Figure 26:
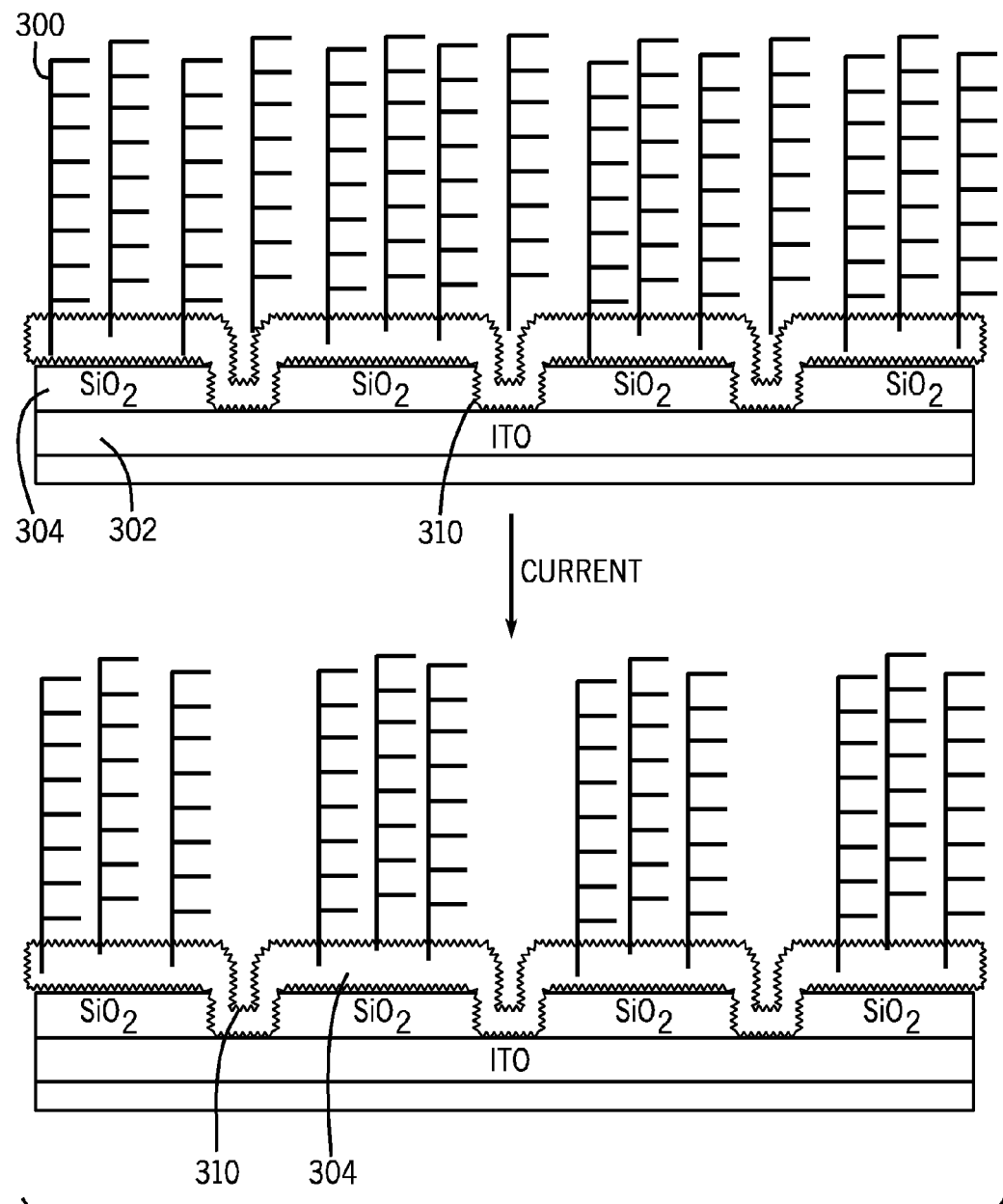
FIG. 26 is a diagrammatical representation of steps in the preparation of primer patterns in accordance with embodiments of the present techniques.

While certain disclosed embodiments related to selectively patterning a surface with appropriate sites 22 (e.g., polymer pads 68), either with or without grafted primers, another approach may involve laying down a surface of polymers with associated primers and then selectively removing, deactivating, decomposing or, otherwise rendering unusable the primers from selected regions of the surface. Further, while the disclosed techniques may be used alone to generate a patterned surface, they may also be used in conjunction with other disclosed patterning techniques (e.g., base pad formation techniques) to yield a complex patterned surface. In one embodiment, electrical fields may be used to selectively decompose nucleic acids at a particular region of a surface, repel nucleic acids from a particular region of a surface or remove nucleic acids from a particular region of a surface to yield a desired primer pattern. The region of the surface from which nucleic acids are decomposed, removed or repelled can be the interstitial regions between the pads where nucleic acids are desired. For example, as illustrated in FIG. 26, an electrical current is applied to a lawn of primers 300. In particular, an electro-active surface 302 (such as, but not limited to, ITO) is decorated with dielectric pads 304 (such as, but not limited to, $SiO_2$) that act as resists. Grafted PAZAM, or other polymer 306, sits atop this surface via covalent or non-covalent immobilization. An electrical current, or voltage potential, is applied through the electrically conductive layer 302, resulting in the removal, ablation or deactivation of the DNA primers present in those regions 310 without dielectric pads 304. Regions shielded by the dielectric pads 304 will retain features of PAZAM, or other polymer, with grafted primers 300.

Figure 27:
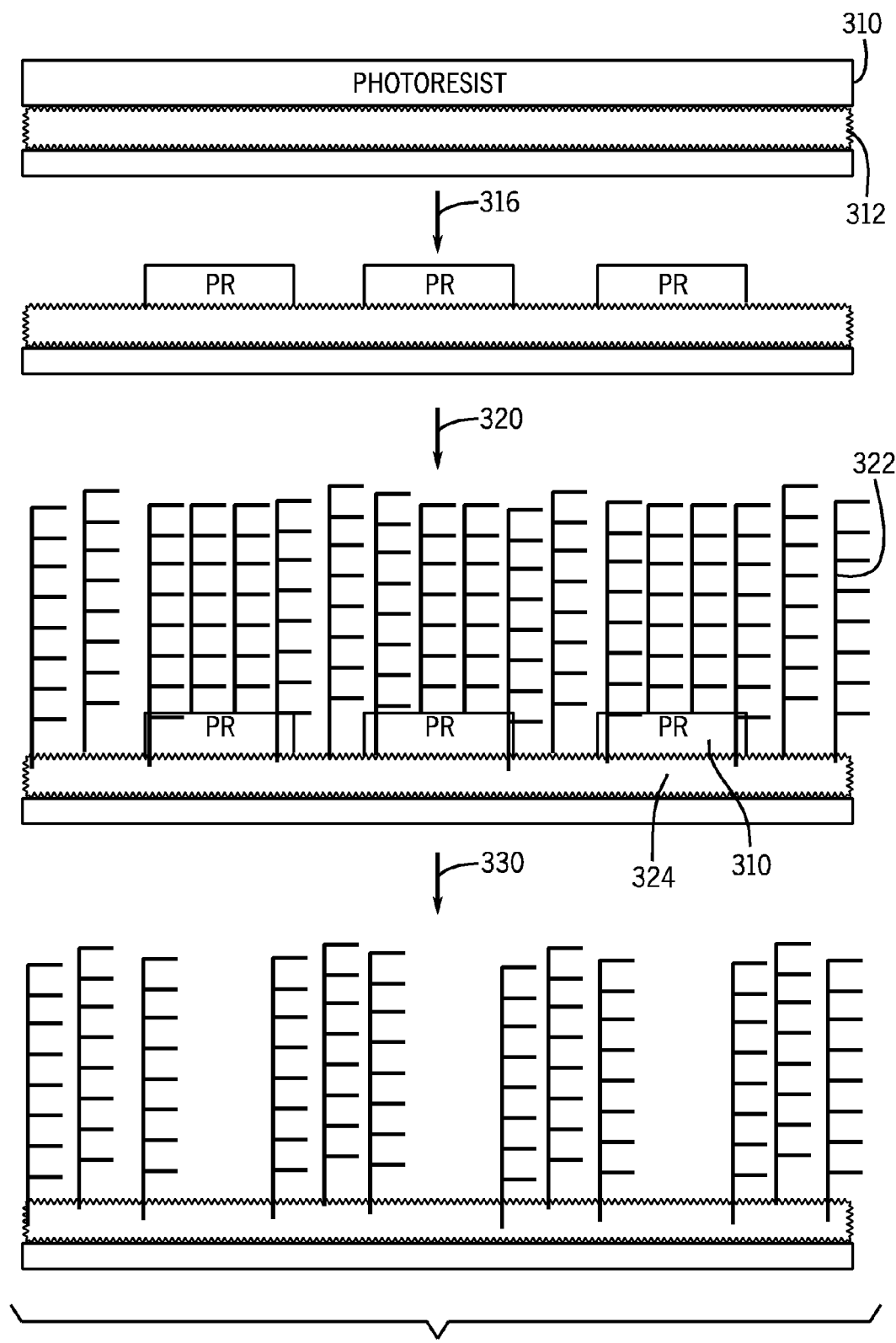
FIG. 27 is a diagrammatical representation of steps in the preparation of base pads in accordance with embodiments of the present techniques.

FIG. 27 illustrates a liftoff approach for patterning primers. A photoresist layer 310, or other patternable substance, is deposited over a reactive layer 312 (e.g., PAZAM, or another polymer). The photoresist layer 310 is then patterned via photolithography, nanoimprint or other viable process at step 316. The primer grafting solution is flowed over the top at step 320, resulting in restricted functionalization and application of primers 322, via homogenous or heterogeneous methods. The patterned photoresist layer 310 protects the interstitial regions 324 of PAZAM, or other polymer, from reacting. Liftoff can then be performed at step 330, leaving patterned areas of grafted primers 322.

Figure 28:
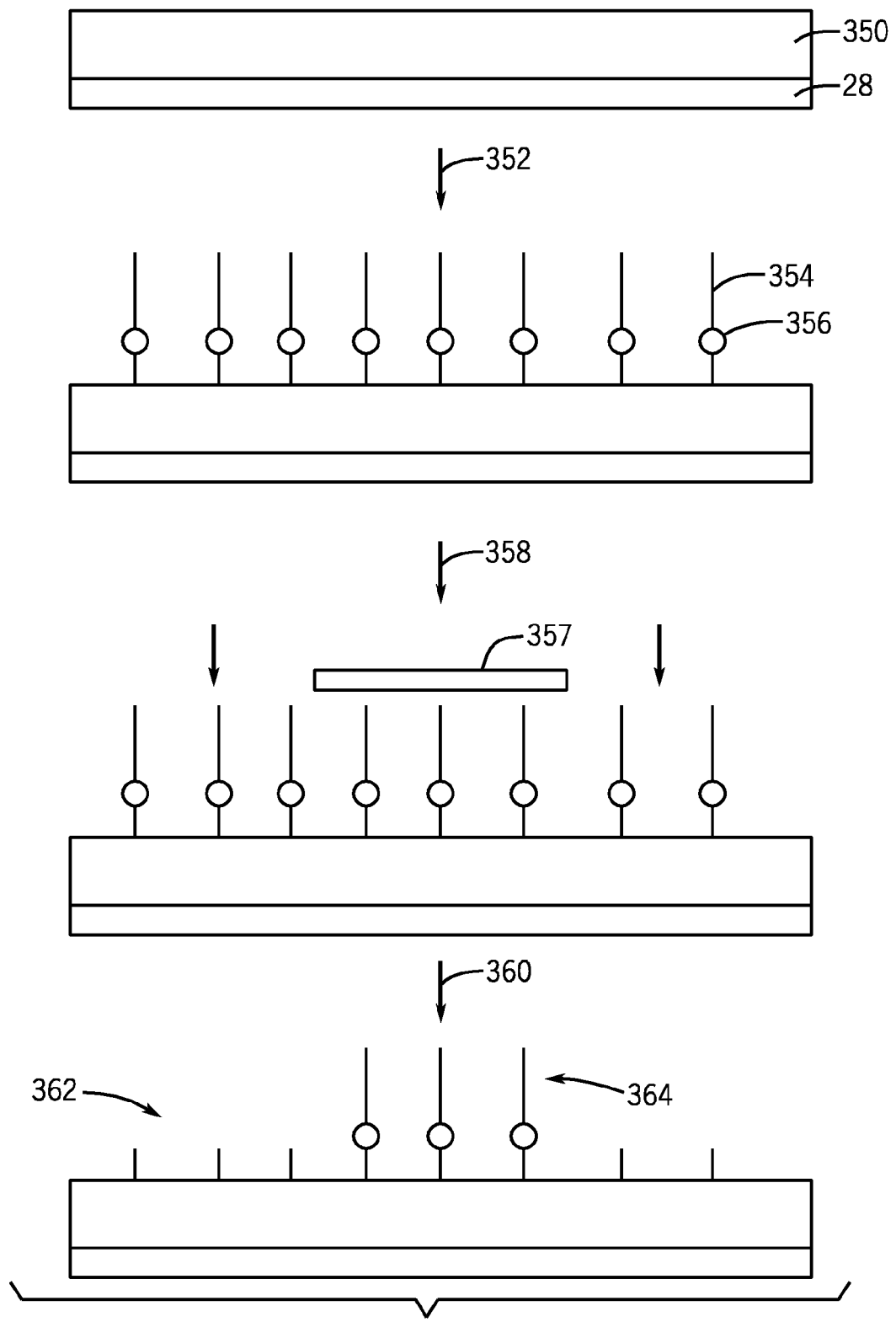
FIG. 28 is a diagrammatical representation of steps in the preparation of base pads in accordance with embodiments of the present techniques.

A number of photoactivated/photocleaved grafting events may be performed to leave grafted primer lawns. In one example, illustrated in FIG. 28, a substrate 28 that includes a photoactivatable covalent coating is seeded at step 352 with photocleavable primers 354. In particular, a photocleavage site 356 may be placed into the DNA and a photomask 357 applied to yield a desired primer pattern at step 358. After irradiation at step 360, after irradiation, those regions not protected by the photomask 357 are cleaved to yield cleaved non-reactive primers 362 and reactive primers 364. Alternatively, in another embodiment reactive primers may be protected by a photocleavable unit. Areas exposed to light are released and made reactive leaving behind reactive primer regions and non-reactive primer regions.

Figure 29:
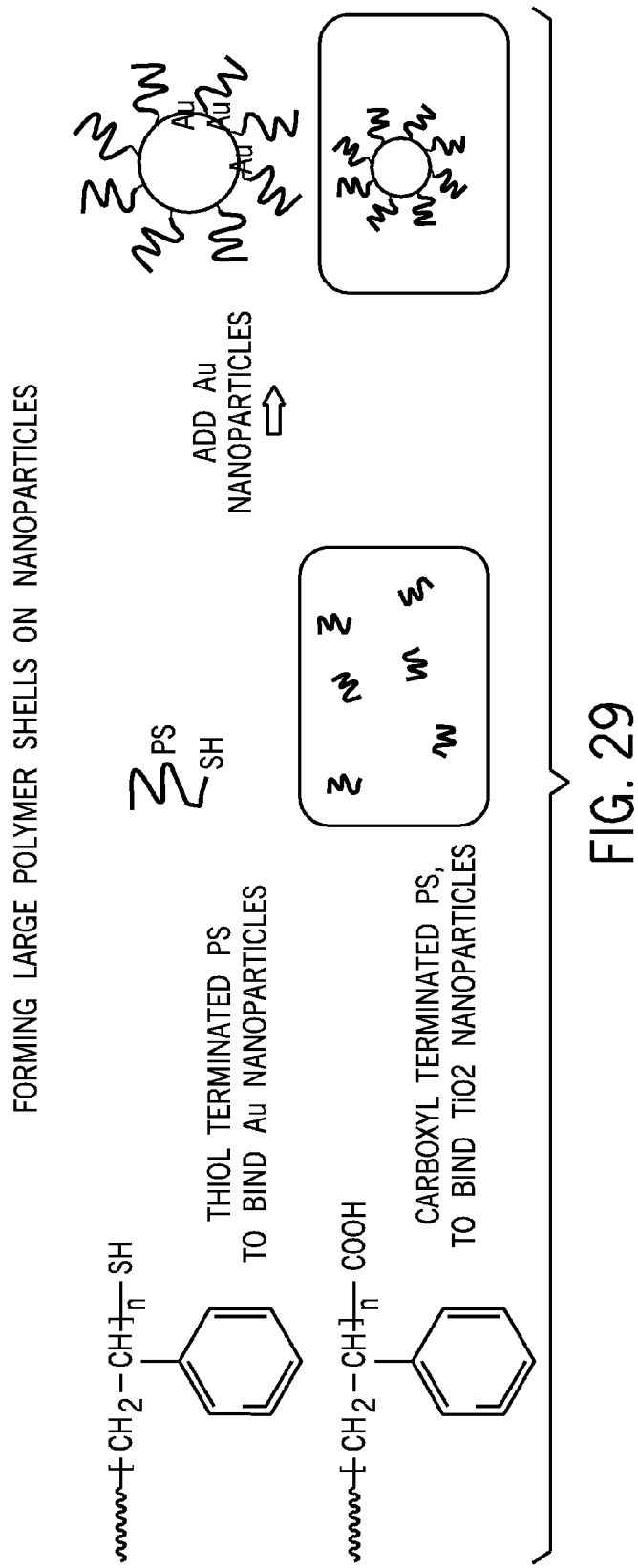
FIG. 29 is a diagrammatical representation of steps in the preparation of nanoparticles in accordance with embodiments of the present techniques.
Figure 30:
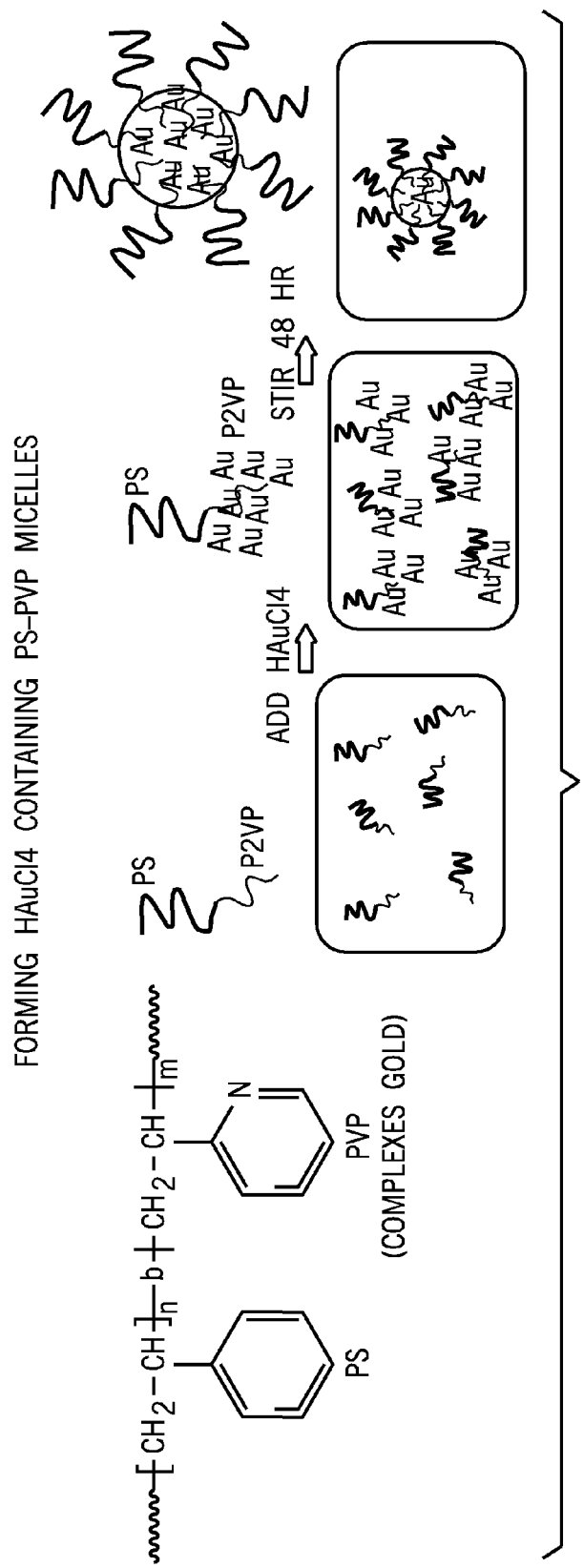
FIG. 30 is a diagrammatical representation of steps in the preparation of nanoparticles in accordance with embodiments of the present techniques.

In another embodiment, nanostructures may be used to faciliate base pad formation. In one aspect, nanodots that are undersized relative to fabricated wells may be modified with a thick padding layer such that the whole structure is of a size that may be loaded singly into wells fabricated by conventional lithography techniques. In one embodiment, nanodots are prefabricated (e.g. via sol-gel reduction, reduction from a salt solution, reduction from a micelle solution etc.) or purchased from a commercial vendor. Long polymers can be attached to these nanoparticles using a specific interaction on one end of the polymer. In certain embodiments, the polymer shell may be made very rigid by chemical crosslinking or by a solvent exchange leading to an entropically locked glassy state. As shown in FIG. 29, for gold nanoparticles, the specific interaction may be to a thiol group present on one end of the polymer. In another embodiment in which titanium oxide nanoparticles are used, the specific interaction may be due to a carboxylic acid termination on one end of the polymer. To increase the size of the polymeric shell, the polymer is added to the nanoparticles in a suitable solvent. In solvent, the polymer is stretched, ensuring both a dense and a thick shell around the nanoparticles. The shell may be crosslinked for stiffness. Any free double bonds may be crosslinked photochemically using light activation of a photochemical crosslinking reagent or moiety, or crosslinked chemically using any of a number of small molecule crosslinking reagents or moieties. Alternately, the nanoparticle-shell solution may be diluted into a non-ideal or theta solvent of the polymer, forcing the dense polymer shell to collapse, resulting in a glassy, sterically locked conformation. It is to be understood that the polymer shell could consist of a homopolymer or multiple-block-copolymers, wherein further, the binding to the nanoparticles could be due to specific interactions with one of the inner blocks of the co-polymer micelle, as shown in FIG. 30. For example, the precursors to nanoparticles, preferrably metal salts or metal alkoxides in a solvent medium can be chelated in the cores of a copolymer micelle. This combines the processes of nanopartice synthesis and deposition, allowing more control over both processes. Briefly, the core of the micelle is a polymer that is able to complex with the metal or is able to sequester the metal solution due to surfactant action protecting it from the solvent. The disclosed techniques may be used to crosslink or stiffen the micelles, if needed.

Figure 31:
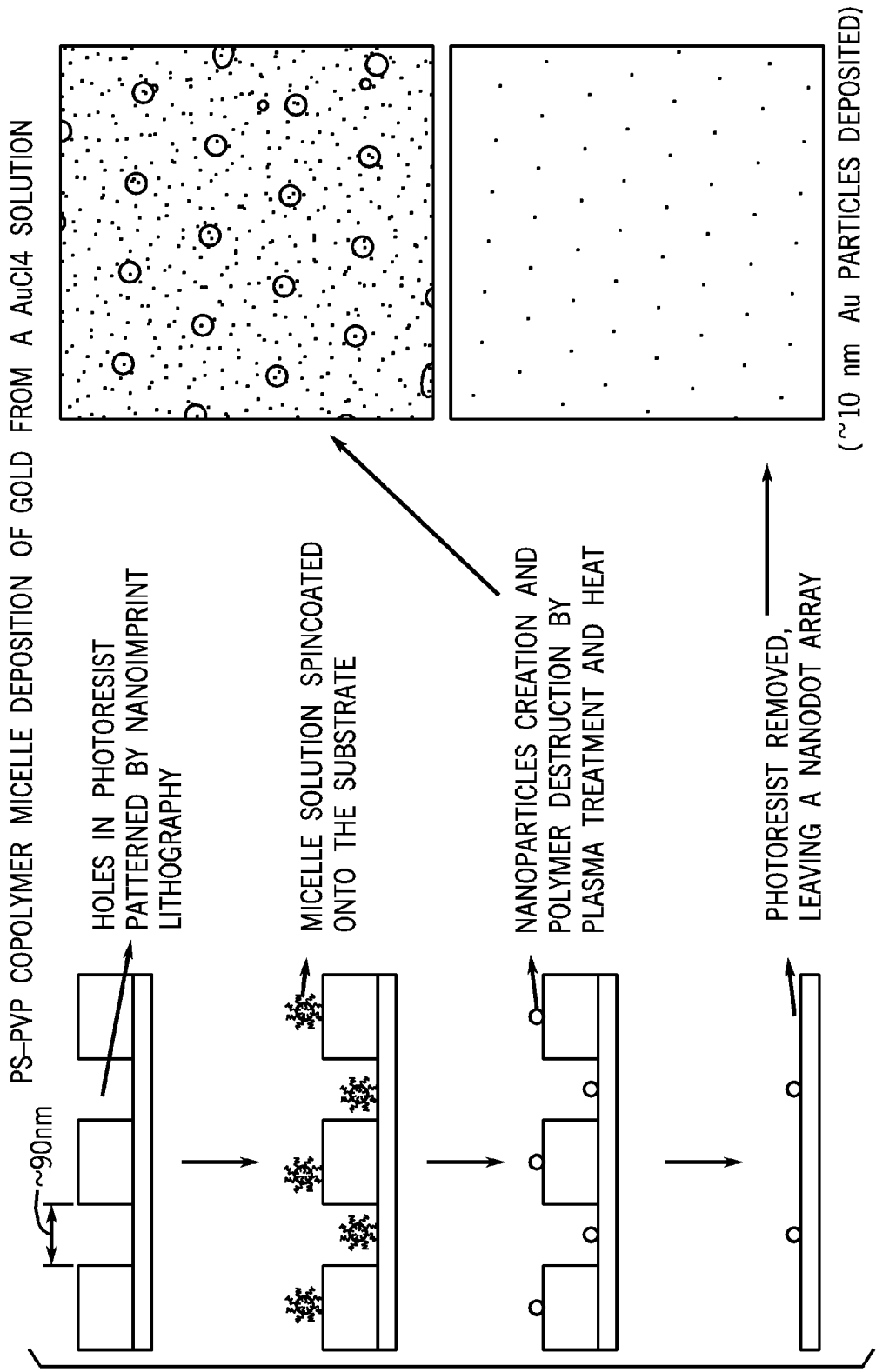
FIG. 31 is a diagrammatical representation of steps in the deposition of micelles in accordance with embodiments of the present techniques.

As shown in FIG. 31, nanoparticle-containing shells, such as those exemplified above, may be loaded in to large photoresist wells on a substrate. Once loaded, the polymer is burned off in a plasma chamber and the photoresist removed in a suitable solvent leaving single nanoparticles in an ordered array. The nanoparticle-precursor containing micelle can be deposited into nanowell arrays by spin coating or dipcoating. Reduction of the metal solution to metal can occur under oxygen plasma or high temperatures, which destroys the polymeric micelle in the process as well. The nanowell arrays are typically produced by standard lithography techniques, wherein one embodiment is nanowells produced in photoresist layers which may be stripped away after the nanoparticle reduction. In addition, passivation techniques may be used in conjunction with the above nanostructure embodiments, or any other disclosed embodiments. In particular, entaglement of library elements to the SFA matrix and the non-specific binding of DNA capture moities (avidin) on the flowcell surface may conrtibute to non-specific background noise. In one embodiment, a diamond-like carbon (DLC) passivation layer is applied to all or part of a flowcell surface. DLC can be easily etched and processed with standard lithography tools. Further, DLC is hydrophobic and biocompatible. The passivation layer can include other materials including. For example, hexa-methyldisilizane, Teflon, fluorocarbons, parylene, perfluorinated polymers, metals, metal oxides, or PEG or other types of passivating polymers.

Figure 32B:
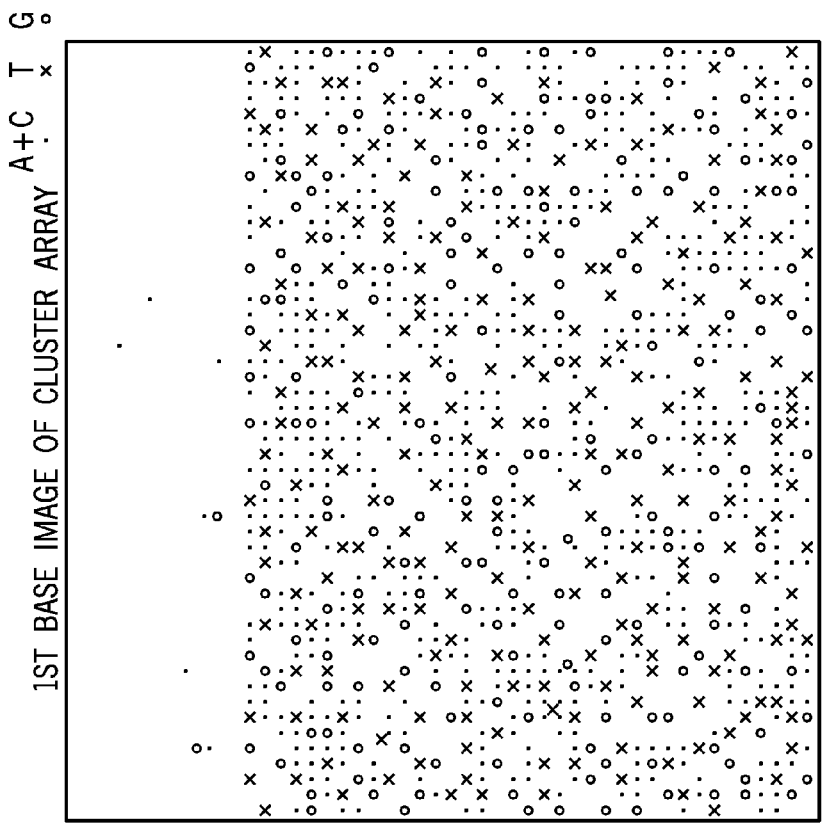
FIGS. 32A and 32B are cluster image data of a diamond-like carbon patterned microarray.
Figure 32A:
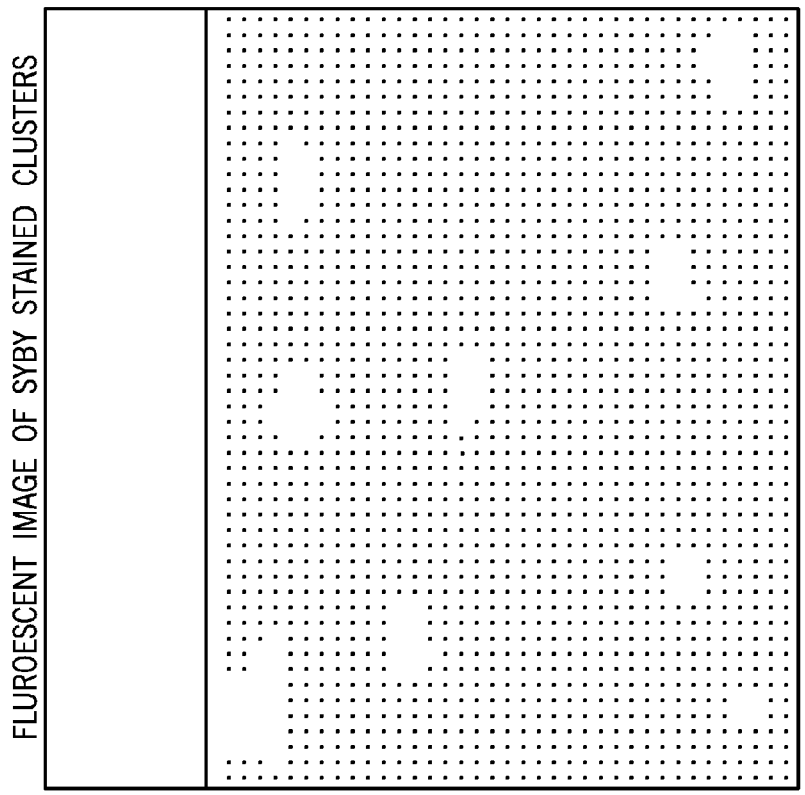

In another embodiment, a DLC film or mask may be used to grow DNA clusters in predetermined positions as well as control the size of the clusters by confining their growth to the size of the patterned feature. The pattern of DLC impedes both DNA templates seeding and amplification. In one example, a 30 nm thick DLC film was deposited on glass flowcell substrates and windows on the DLC film were opened only at desired positions. Using the DNA seed-through biochemistry process, DNA templates were only seeded in the windows in the DLC film, and the DNA clusters were confined within the window area after bridge amplification process. FIG. 32A shows a fluorescent image of SYBR Green-stained cluster formed on a DLC-patterned substrate, and FIG. 32B shows a $1^{st}$ base image of the cluster array of FIG. 32B.

This DLC based cluster growth control system faciliates patterning of highly ordered cluster arrays that increase area cluster density and simplify signal analysis processes to boost the sequencing throughput. The DLC can also be applied to existing flowcell products more generally to deplete the unwanted cluster growth; for example, on the top channel surfaces for one-side imaging system. Besides the glass, the DLC can also be patterned on different dielectric substrates such as $Si_3N_4$ or $SiO_2$ coated Si substrates.

Figure 33:
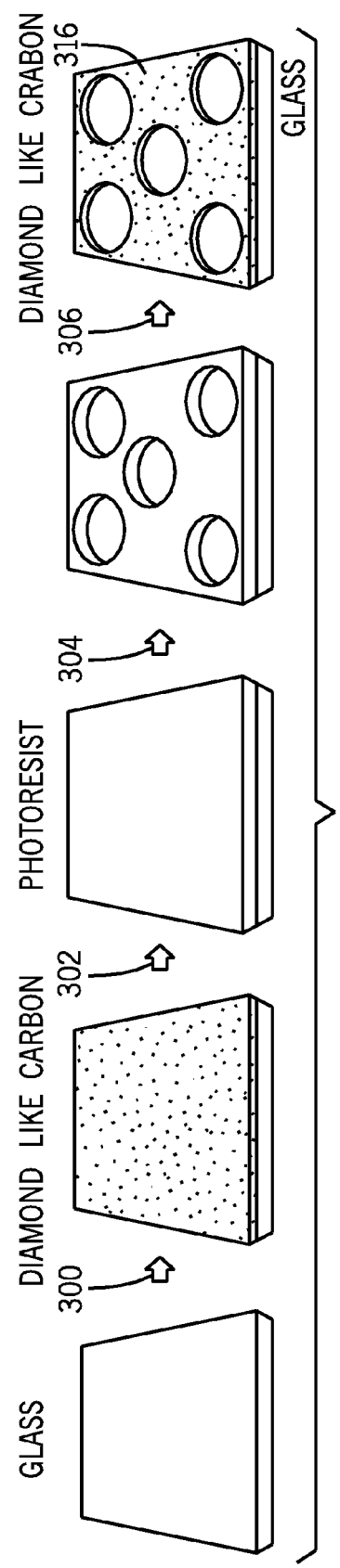
FIG. 33 is a diagrammatical representation of steps in the preparation of a diamond-like carbon passivation layer in accordance with embodiments of the present techniques.

In one example, illustrated in FIG. 33, a DLC film is made at step 300. The film can be made by plasma enhanced chemical vapor deposition (PECVD) onto glass, which may include systems with methane ($CH_4$) as the gas source. After application of a photoresist layer at step 32, etching at step 304, and liftoff at step 306, a patterned DLC layer 310 may be formed. In addition, the surface energy of the DLC film can be tailored by adding CF compound gas during PECVD. Chemical surface modification of DLC by using 3-Aminopropyltriethoxysilane (APTES) can also be used in DLC patterned flowcells.

Figure 34A:
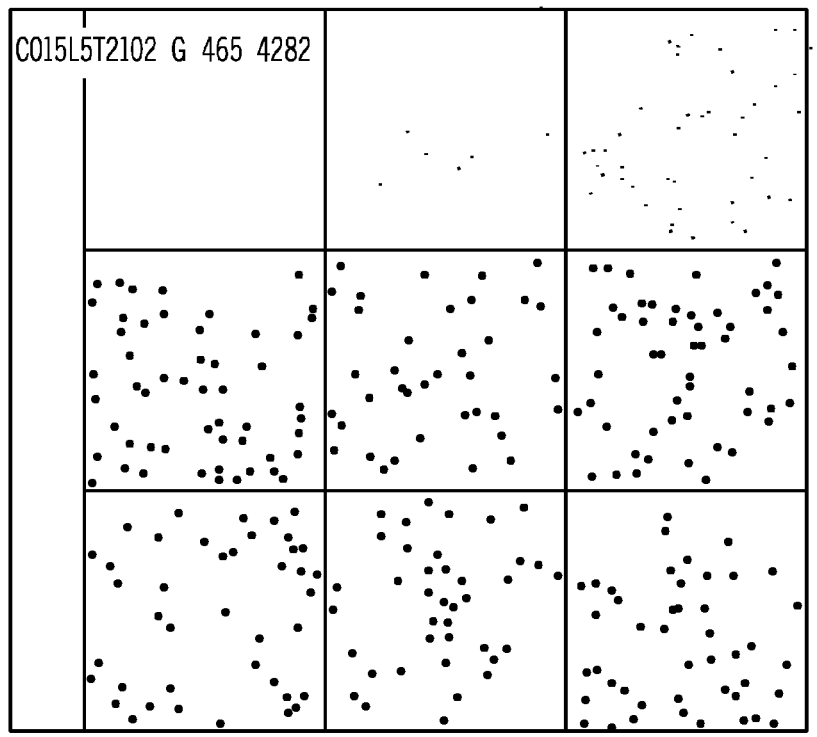
FIG. 34A and FIG. 34B illustrate PEG molecular crowding results with and without PEG.
Figure 34B:
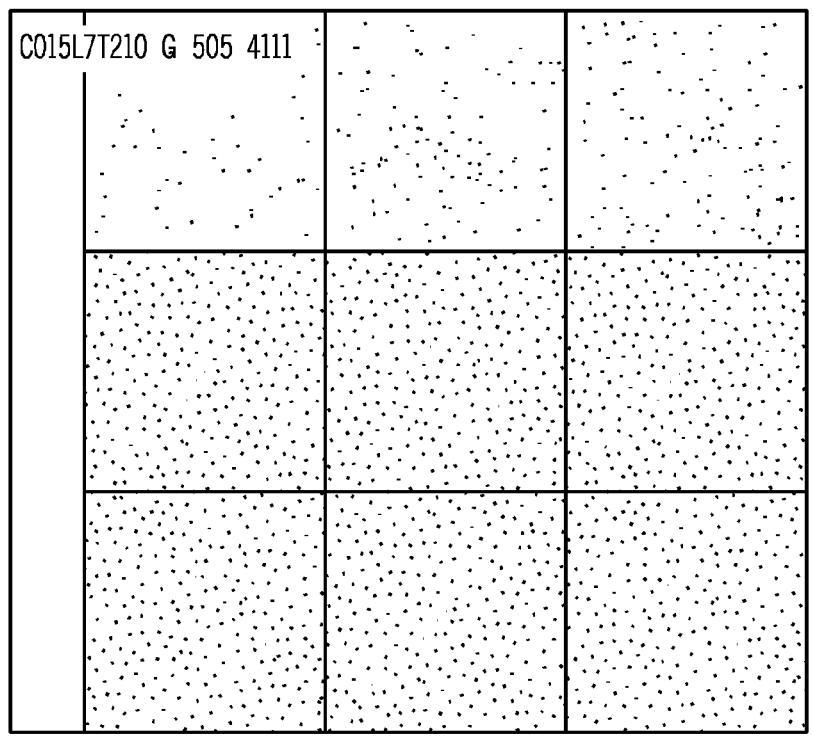

In addition to patterning techniques, improved binding performance for any type of sequencing or other biological reaction, such as those disclosed herein, may be achieved by altering the characteristics of the reaction solution or the reaction conditions to encourage molecular crowding, which may result in enhanced binding at the sites 22. In one embodiment, the disclosed substrates and arrays may be used in conjunction with molecular crowding techniques. Briefly, when two macromolecules are mixed in a solution, the free energy of mixing promotes the miscibility of the two populations whereas the translational entropy is maximized when the two components are phase separated. If one of the components of the mixture is capable of restricting the free motion of the second component, the depletion interaction is pronounced, leading to domains of like-molecules with greatly increased local concentrations. Adding suitable concentration of PEG solutions of an appropriate molecular weight may concentrate template molecules within the flowcell leading to an enhanced rate of capture at the sites 22. FIG. 34A-B show results from an experiment in which PEG was used to improve seeding efficiency for avidin and biotin-labeled DNA interaction. In both the control and the PEG crowded run, 0.015 mg/ml of avidin was non-specifically bound to the surface of an unpatterned flow cell. Biotin-labeled (i.e., P5 end labeled) DNA was contacted in the absence of (FIG. 35A) and presence of (FIG. 35B) 5% PEG 8000 solution. Images were taken of clusters from a G channel acquisition on a HiSeq 2000 (Illumina, Inc., San Diego Calif.). Without PEG, as shown in FIG. 34A, the run achieved 98.3% alignment with 95.6% rate pass filter and about 200K/mm2. With PEG, as shown in FIG. 34B, the run achieved 95.2% alignment with 83.4% rate pass filter and greater than 900 K/mm$^2$. The reaction with PEG exhibited greater cluster density. Accordingly, it is contemplated that the present techniques may incorporate PEG or other reaction solutions that faciliate molecular crowding. In one embodiment, the substrates and/or microarrays disclosed herein may be used with about 1%, 2%, 3%, 4%, 5%, 6%, 7%, 8%, 9%, 10%, 25% or 50% PEG. Further, PEG may be present in the reaction solution or the flowcell solution in ranges of about 1%-10%, 1%-8%, 1%-3%, 3%-5%, or 5%-10%, 1%-25%, 1%-50% or 10%-50%.

In another embodiment, electrophoresis may be used to concentrate DNA molecules close to the surface. In one implementation, a transparent conductive layer such as indium tin oxide (ITO) is coated on the top and bottom surfaces of the flowcell such that the ITO surfaces function as electrodes. An applied electric field drives the DNA molecules towards the surfaces/electrodes, where they are specifically immobilized to the capture pads. Over time the DNA molecules adhere to the surfaces non-specifically, whereas in the absence of the field, no such surface accumulation and adsorption is seen. In addition to ITO surfaces, other type of electrically-conductive surfaces may be appropriate for encouraging molecular movement towards the substrate 28, such as oxide or polymer surfaces. Exemplary surface materials include, but are not limited to, $SnO_2$, aluminium-dope ZnO (AZO), ZnO, $TiO_2$, Poly (3,4-ethylenedioxythiophene (PEDOT), and the like. In one embodiment that uses a oscillating electric field, the DNA molecules concentrate to the top and bottom surfaces cyclically. The oscillating field provides an additional benefit of reducing electrolysis and mimicking electrochemisty at the surfaces.

Figure 35:
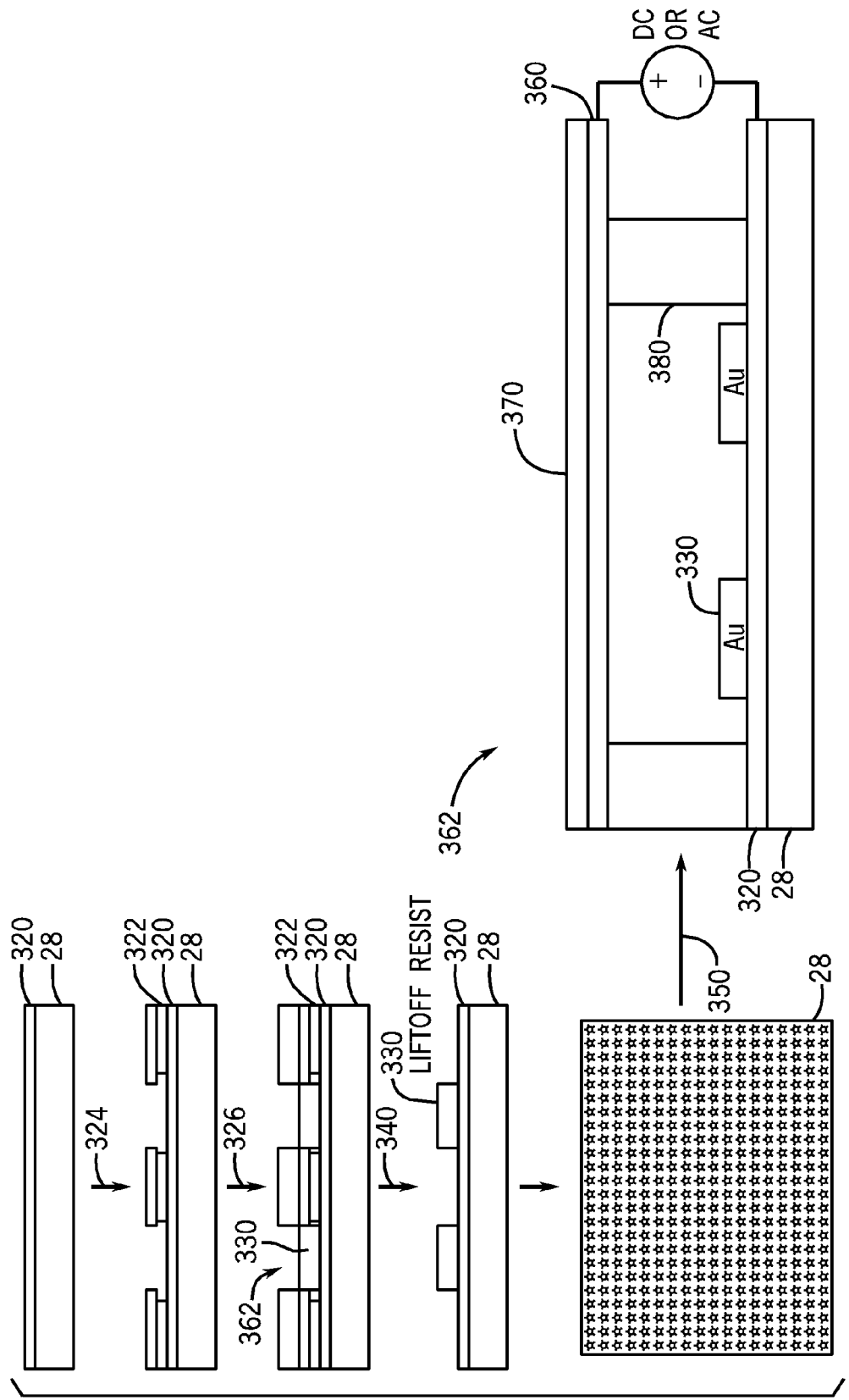
FIG. 35 is a diagrammatical representation of steps involved in concentrating DNA via an electrical field in accordance with embodiments of the present techniques.
Figure 36:
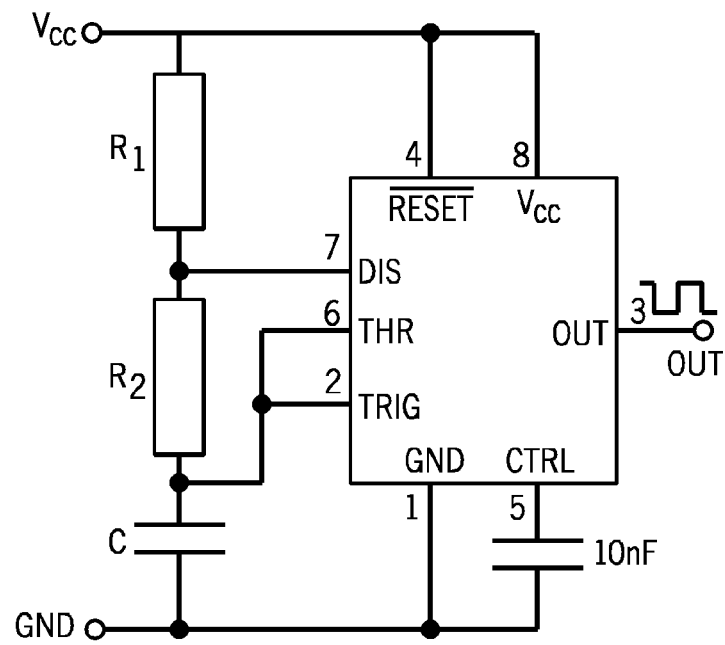
FIG. 36 is an exemplary circuit that may be used with an electrically conductive flow cell
Figure 37:
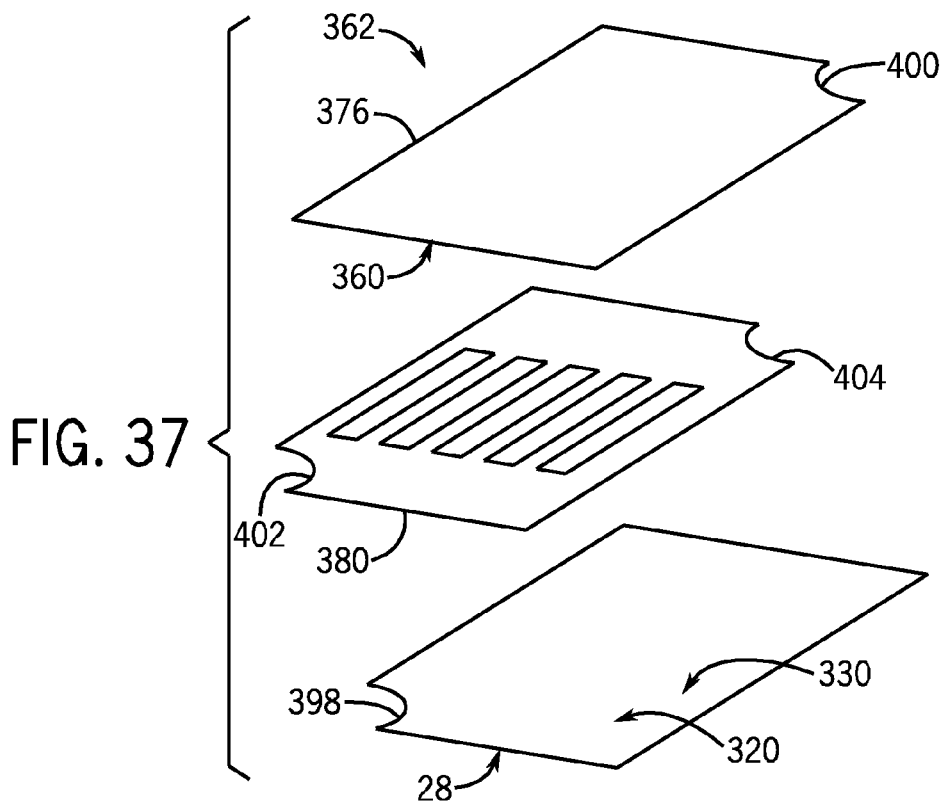
FIG. 37 is an exploded view of a flow cell including an electrically conductive layer in accordance with embodiments of the present techniques.

FIG. 35 illustrates a workflow for creating gold pads on an ITO surface. After evaporation of ITO to form an ITO layer 320 (e.g., 200 nm thick) on the surface of the substrate 28, a double-layer resist 322 is spin-coated into the ITO layer 320 and etched at step 324. The double-layer photoresist layer 322 may be used to achieve clean edges of the pads. Ti/Au deposition, for example via evaporation, is performed at step 326 to yield an Au layer 330 in the interstitials 332 of the photoresist layer 322. In one embodiment, the Au layer 330 may be about 60 nm or less while the Ti layer may be evaporated to about 4 nm or less. Following a liftoff at step 340, the substrate die 28 can be patterned according to a desired pad size and pitch. At step 350, the Au-patterned substrate die 28 and a plain ITO surface 360 are sandwiched into a flowcell 362, which may include appropriate casing and spacer components, such as outer layer 370 and spacers 380. A 4 volt peak-to-peak (+2 to −2) voltage at 0.5 Hz can be used to draw the molecules towards the top and bottom surfaces cylically. FIG. 36 is a circuit diagram of an exemplary circuit that may be used to provide AC signal to the flowcell 362. FIG. 37 is an exploded view of the flowcell 362. As shown, the substrate 28 and the outer layer 370, which, in certain embodiment, may be glass and/or the same material as the substrate layer 28, have respective notches 398 and 400. As illustrated, the notches are at opposing corners. However, it should be understood that the notches may be positioned in any suitable location to permit access to the ITO layer 360 and the ITO layer 320 so that AC power may be supplied across the flow cell 362. Similarly, the spacer 380 also may include notches 402 and 404 that are aligned with notches 398 and 400, respectively.

Figure 38:
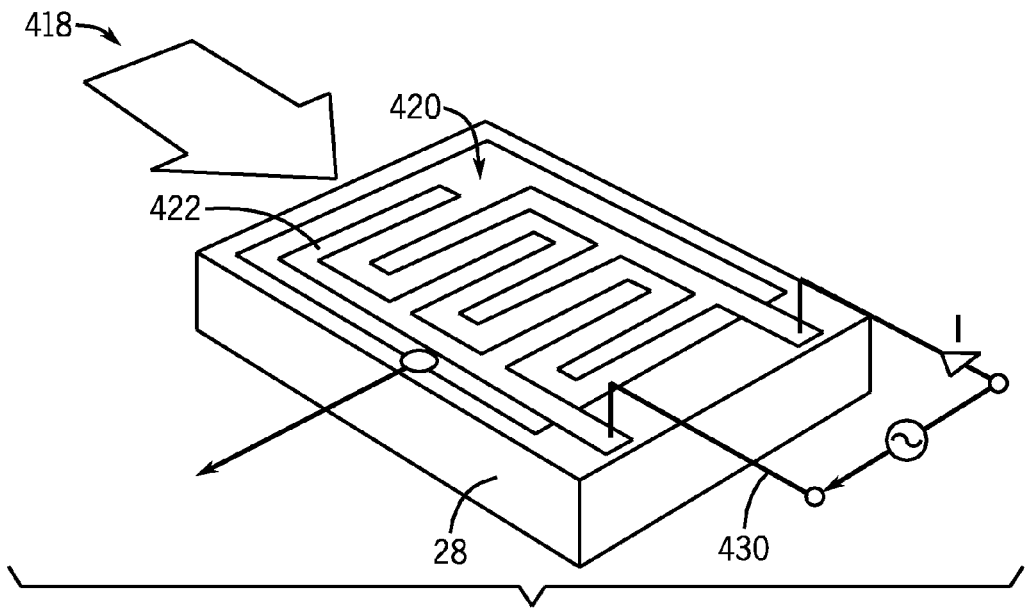
FIG. 38 is a perspective view of a flow cell configured for dielectrophoresis in accordance with embodiments of the present techniques.
Figure 39:
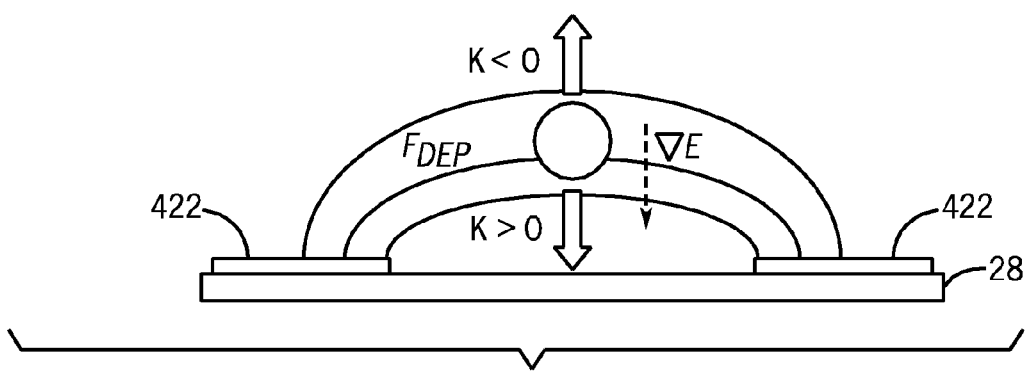
FIG. 39 is a schematic diagram of electric fields generated by the flow cell of FIG. 39.

In addition to transverse electrical pulldown, a longitudinal time-varying electric filed across interdigitated electrodes may also be used to concentrate DNA by dielectrophoresis. Dielectrophoresis is sensitive to mass. Therefore, a size-dependent pulldown of DNA can be achieved by manipulating the dielectrophoretic force. The dielectrophoretic force increases by decreasing the spacing between the interdigitated electrodes and also by increasing the applied field and frequency of oscillation. Large molecules experience larger forces at low field and frequency, while smaller molecules are pulled down by larger and high-frequency oscillating fields. A DEP based pulldown can remove the need for size selection of libraries while also allowing applications such as pulling down protein-bound DNA to the surface selectively (for example, to accommodate real-time field-sorted chromatin immunoprecipitation sequencing (CHIPSeq)). FIG. 38 is an example of a flow cell configuration that may be used for DEP. The flowcell 418 includes passive areas 420 separating a serpentine electrode 422 that are applied to the substrate 28. The electrode is powered via a voltage source 430. FIG. 39 is a schematic illustration of the generation of dielectric forces between the areas of the electrode 422.

As discussed herein, the microarrays disclosed herein facilitate binding and/or amplification of a single molecule (e.g., steric exclusion or kinetic exclusion such that only one molecule is copied at each pad or feature of an array). Typically the patterns contain a DNA capture moiety and the DNA molecules contain a binding moiety (e.g., streptavidin incorporated into base pads and biotin on the DNA). If the number of binding moieties on the DNA is equal or greater than the number of capture moieties on the pad, one, and only one, DNA molecule can bind to a pad. This is in addition to steric repulsion, which can itself help in reducing multiple bindings to the same pad. In certain embodiments, capture of template DNA molecules is a two stage process. For example, avidin molecules are first immobilized onto gold pads via thiol bonds and DNA containing biotin on one end are captured by the avidin on the gold pads. There are four biotin binding sites per avidin, and there are multiple avidins per gold pad. Steric hindrance may prevent multiple DNA molecules from binding to the same gold pad. Steric hindrance is improved if the sites (e.g., base pads 68) are very small. However, there is a possibility of inducing multiple bindings per pad. One technique to ensure clonality of seeding is to ensure the first DNA molecule that binds to a pad is able to saturate all the DNA-capture-moieties on the pad.

Figure 40:
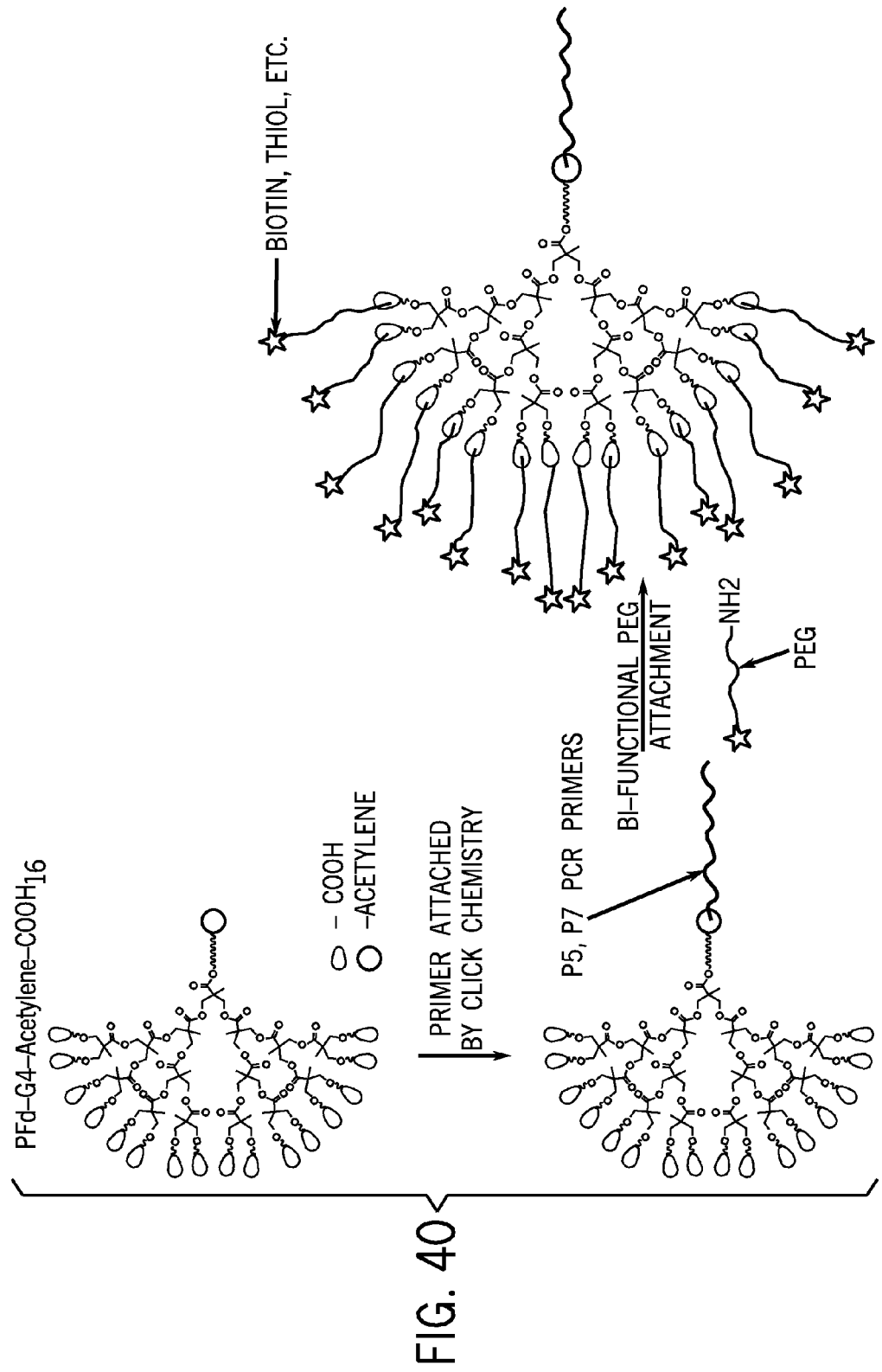
FIG. 40 is a diagrammatical representation of steps involved in generating primers with dendron termini in accordance with embodiments of the present techniques.

In one embodiment, multidentate ligands or receptors may be used to increase the number of binding moities on DNA that binds to a pad. Exemplary multidentate ligands or receptors that can be used include, but are not limited to, dendrons, avidin, streptavidin and functionally active derivatives thereof. In one embodiment, a dendron (or other multidentate ligand or receptor) is incorporated into the library through a PCR primer or through a transposome complex in the case of PCR free libraries such as those used in TruSeq Nextera protocols available from Illumina Inc. (San Diego, Calif.). Either P5, P7 or both P5 and P7 can be modified with a dendron (or other multidentate ligand or receptor) on their 5' end (e.g. 5' azide followed by click reaction with acetylene on the Dendron). Multidendate ligands or receptors with —COOH moieties can directly bind to $TiO_2$, ZnO, $Al_2O_3$, and ITO nanodots. The carboxyl group can be converted to a biotin or thiol using a bifunctional PEG linker. Further, the reach of the arms of the ligands or receptors can be increased by adding PEG spacers, allowing a single template molecule to access/bind-to a large surface area of the capture pad via the multiple receptors or ligands. A thiol terminated dendron (or other multidentate ligand or receptor) can be used to directly bind to the gold pads without needing the intermediate avidin layer. As shown in FIG. 40, a commercially available dendron is attached to a primer and is then converted to include a desired end group (biotin, thiol, etc.). An advantage of using multidentate ligands is increased stability (exponential with addition of binding groups) and increased kinetics of seeding of DNA on pads compared to use of single ligands.

Particular embodiments, involve using mulitidentate ligands or receptors engineered into avidin and DNA. These constructs can be used to seed DNA to a pad directly or via a sandwich avidin/biotin DNA construct. These methods take advantage of the increased avidity and binding stability in metal-ligand interactions (ZnO, ZnS, Gold) with multidentate ligands. Alternatively or additionally to carboxylic acid moieties in multidentate ligands set forth above, multiple thiols, phosphines, phosphine oxides, or amines ($NH_2$) can be used to bind nucleic acids to pads. Such moieties can be incorporated into nucleic acids, for example, by using chemically modified primers to produce modified amplicons in a PCR reaction or by chemical modification of nucleic acids using known chemistries such as N-hydroxy succinimide (NHS) reactions. In addition to dendrons, multi arm PEGs (e.g having greater than 2 arms) can be used to covalently link binding groups to nucleic acids. Proteins such as avidin or streptavidin can be attached to nucleic acids via NHS reactions reactions.

Multidentate lignads and receptors can be used in combination with electric field assisted seeding of nucleic acids to pads. For example, multidentate ligands or receptors may be used to increase the number of binding moities on nucleic acids that binds to a pad and an applied electric field can be used to drive the nucleic acid molecules towards the surfaces/electrodes, where they are specifically immobilized to the capture pads via the multidentate ligands or receptors.

Figure 41:
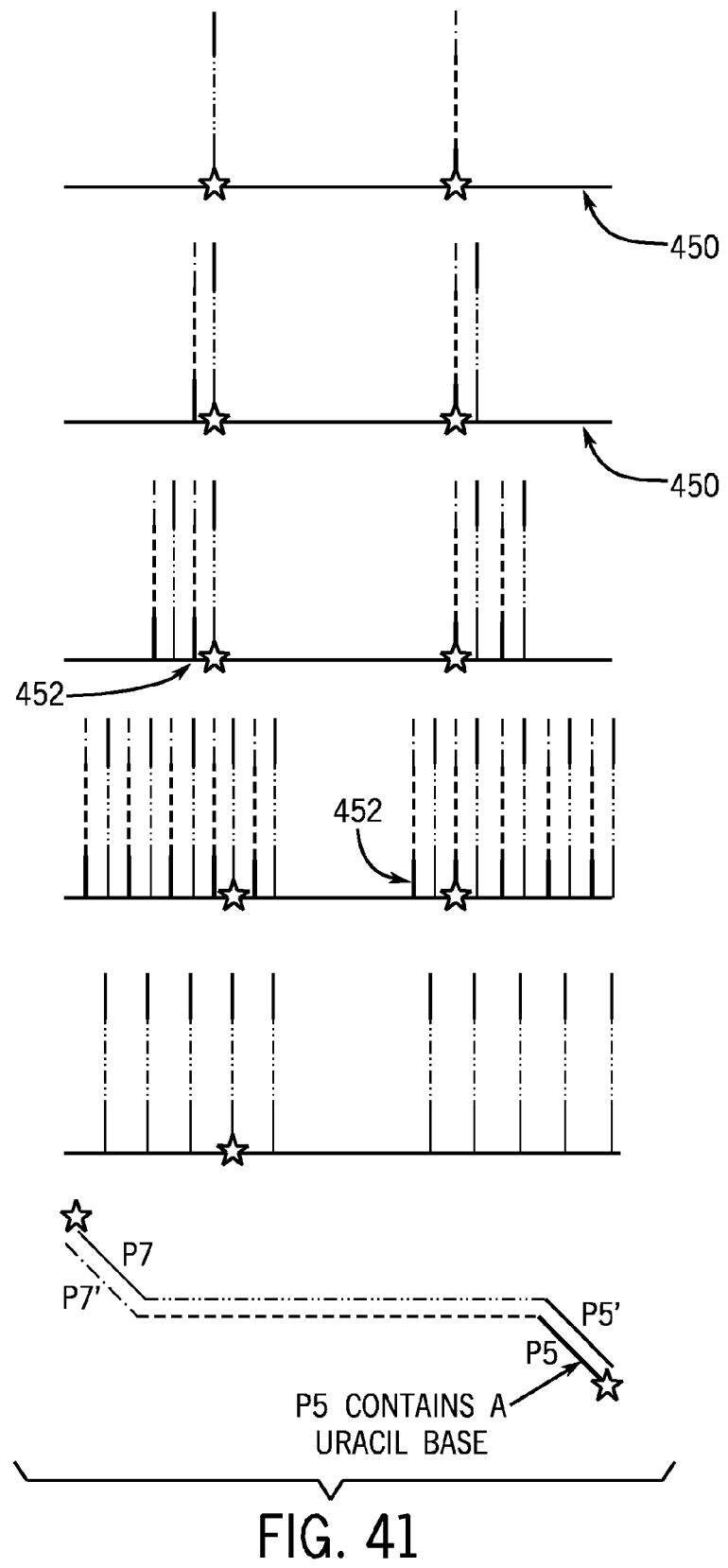
FIG. 41 is a diagrammatical representation of steps involved in forming clusters with primers captured at both ends in accordance with embodiments of the present techniques.

In an alternative embodiment, amine-labeled nucleotides in the primer can be functionalized with an NHS-PEG. Adding binding moities to both ends of the template molecules is another way to improve clonality (i.e. homogeneity of amplicons at an individual pad or feature of an array). As shown in FIG. 41, capturing from both ends of the template may reduce the number of cycles needed to form clusters of a given size. As shown, the primer lawn includes primers that terminate with a characteristic sequence at one end and a different characteristic sequence at the other end. The difference characteristic sequences may include those available from Illumina, such as the P5 adapter and the P7 adapter, which form a primer lawn 450. In one embodiment, the primer terminates with P5 at one end and P7 at the other. After cluster seed formation, self-repelling clusters form because the cluster seeds are complementary strands. In each cluster, the complementary strand of the cluster seed has a P5 anchor, including a U, shown as region 452. Specific cleavage of the P5 results in clonality. The sequences for P5 and P7 adapters are set forth in Bentley et al., Nature 456:53-59 (2008) and WO 00/31148, each of which is incorporated herein by reference in its entirety.

Figure 42:
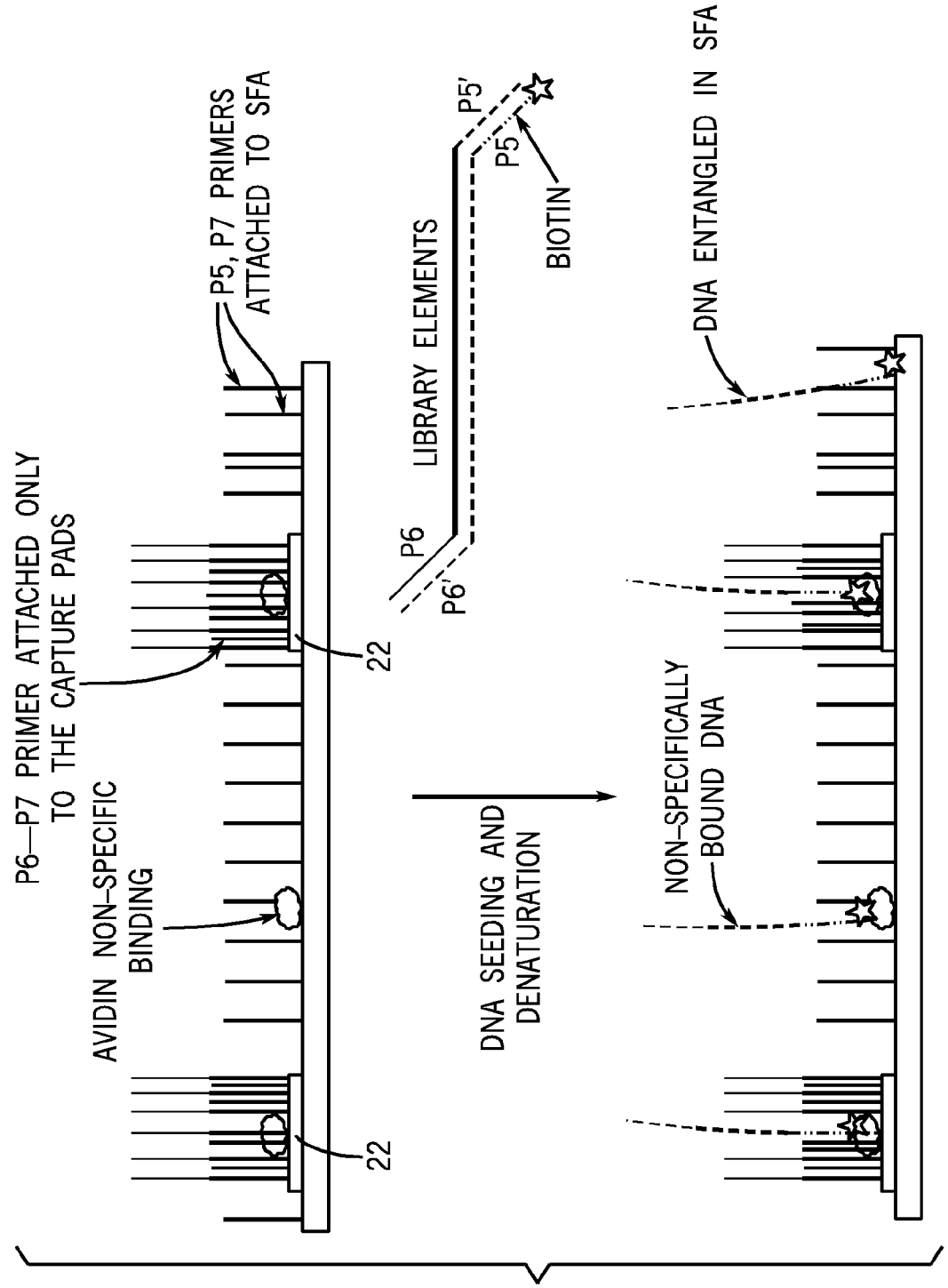
FIG. 42 is a diagrammatical representation of steps involved in forming sites with characteristic end primers and interstitial spaces with primers with different characteristic end primers.
Figure 43:
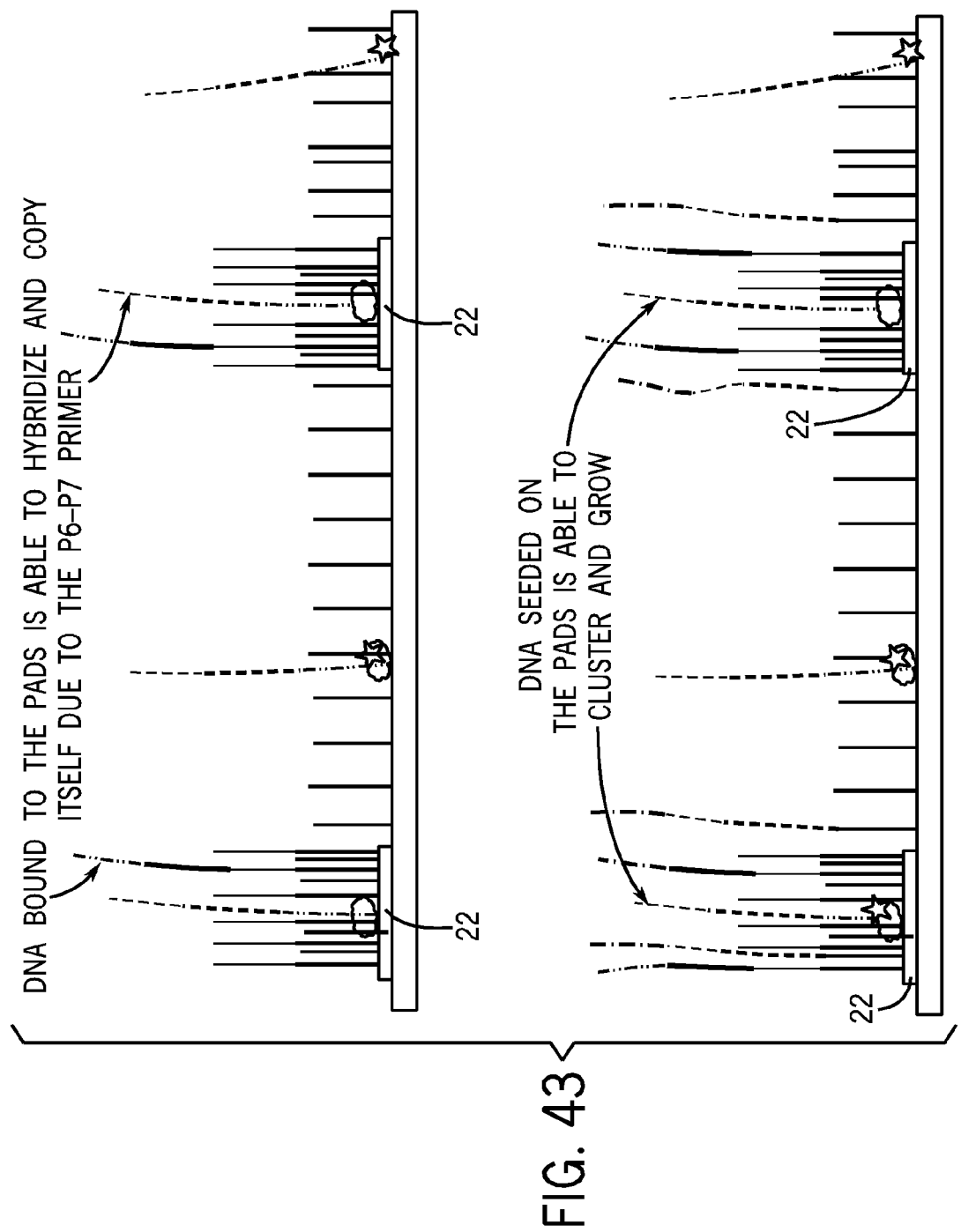
FIG. 43 is a diagrammatical representation of cluster formation in the sites of FIG. 43.

Even if the DNA and/or avidin bind non-specifically, if any clusters that form only grow around the sites 22, the issue of non-specific clusters can be avoided. In the embodiment shown in FIG. 42, the end sequences of the template are P5 and P6. These templates cannot cluster on the SFA lawn which contains immobilized primers P5 and P7. A 'P6-P7' primer is immobilized on sites 22. This primer allows hybridization-extension-copy of the captured template by providing a complement to the 5' end of the molecule which is not present elsewhere on the SFA matrix. This primer also provides the P7 anchor needed for continued copy and clustering cycles that can proceed on the SFA matrix around the sites 22 (e.g., a nanodot site). The P6 sequence may be an SBS sequencing primer (e.g., SBS3). This method provides a robust and simple process to avoid non-patterned clusters of any kind. For the case of SFA-entangled DNA that is not necessarily bound to any avidin or a binding moiety, a 5' exonuclease such as lambda exonuclease may be used to chew back from the 5' end of the DNA. For molecules bound to the capture pad or biotin, the 5' end will not be accessible to the nuclease because the binding/capture occurs from the 5' end of the molecule. As shown in FIG. 43, DNA at the sites 22 is able to form a cluster while DNA in the interstitial spaces does not form any clusters. The sequences for the primers and other oligonucleotides identified above are set forth in Bentley et al., Nature 456:53-59 (2008) and WO 00/31148, each of which is incorporated herein by reference in its entirety.

Figure 44:
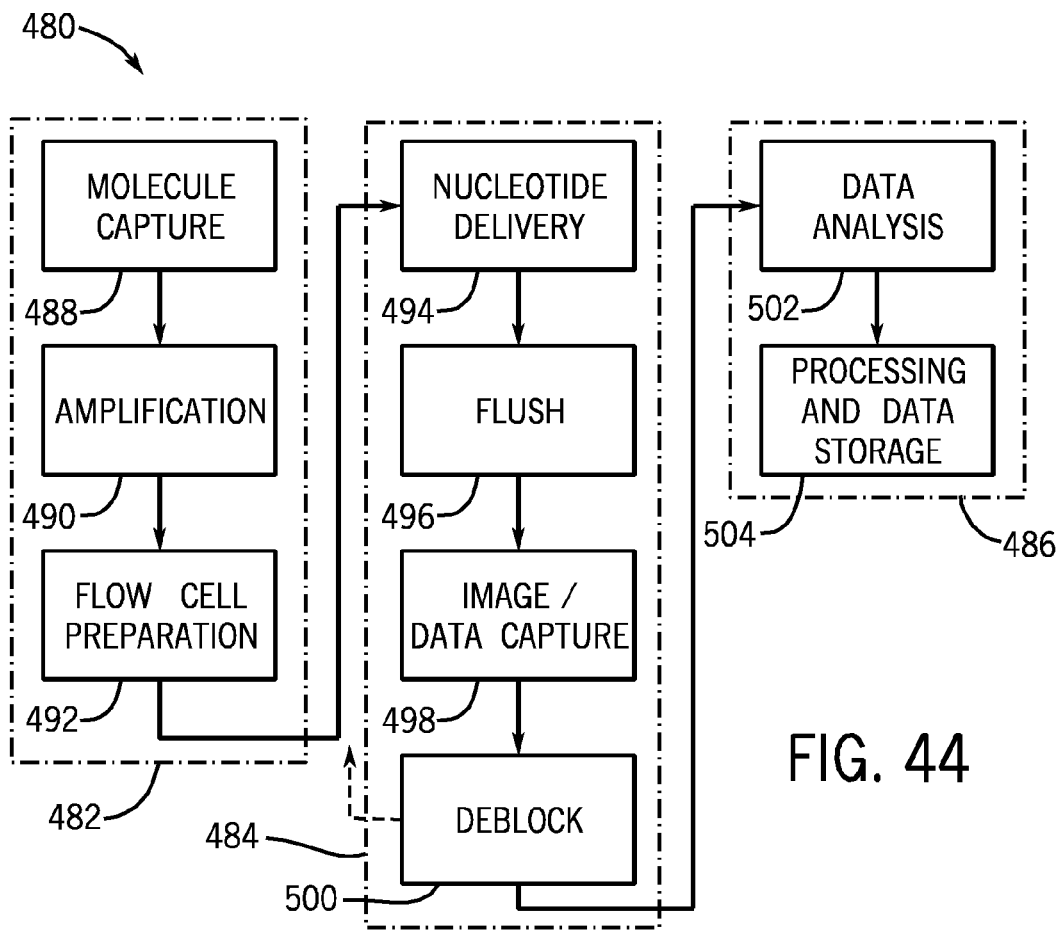
FIG. 44 is a flow chart illustrating exemplary steps in the use with an exemplary microarray.

FIG. 44 illustrates system components generally in an overall system 80 for making, preparing and utilizing microarrays of the type described, along with certain operations performed by the system components. The system may be considered to include an array preparation system 482, an array reading system 484, and an analysis system 486. These three systems may be present as components of a larger system as exemplified in FIG. 44. Alternatively one or more of systems 482, 484 or 486, or components thereof may be present in separate systems. Furthermore, various components exemplified in FIG. 44 may be optionally omitted in some embodiments. The preparation system may begin with a microarray of the type described above, adapted for capture of a molecule at each site. Moreover, as mentioned above, the microarray will typically be disposed in a flow cell, and in certain embodiments, more than one surface within the flow cell may be configured to receive molecules of interest at the sites provided.

As indicated at step 488, then, the exemplary system may be operated to allow for molecule capture. This process can involve flowing a desired concentration of the target molecules through the flow cell in which the array is positioned. In certain presently contemplated implementations, for example, segments of DNA or RNA may include primers at either end, with an attachment molecule, such as biotin secured to at least one of the primers. Owing at least in part to the small size of the sites, and possibly to other effects, such as steric and charge hindrance, each site will preferably only attract and/or attach a single molecule. However, in other embodiments, the sites may be generally larger and may be capable of capturing a plurality of molecules. As noted above, the capture substance provided at each site serves to hold the molecule of interest. The molecules are then amplified, as indicated at step 490. While several different amplification techniques may be utilized, in a presently contemplated implementation, bridge amplification is particularly useful. This and other amplification techniques may be carried out using techniques known in the art as described in references set forth previously herein. Amplification allows for a large number of identical molecules to be co-located at each site, thereby significantly improving the robustness of the subsequent processing, and enhancing signal-to-noise ratios. The flow cell may then be prepared for imaging and analysis, as indicated by reference numeral 492. This process will typically involve connecting the flow cell to inlet and outlet conduits for the flow of nucleotides or other chemistry, as well as for the flow of deblocking agents, flushing agents, and so forth. The flow cell may also be positioned in a processing/imaging arrangement that forms part of the reading system 484. Such may provide for fully or semi-automated, and where desired, cyclic processing and imaging of the sample. Such systems are described in U.S. Pat. No. 7,329,860; U.S. patent application publication nos. US 2010/0111768 A1, or 2011/0220775 A1; or U.S. Ser. No. 13/273,666 or 13/006,206, each of which is hereby incorporated by reference in its entirety.

The reading system 484 may employ a bio-molecule reagent delivery system for delivering various reagents to a sample as it progresses through the system, as indicated by reference numeral 494. The particular configuration of such systems, their degree of automation, the number of cycles the sample may be imaged, and the particular chemistry involved will, of course, depend upon the nature of the molecules being evaluated, as well as the system design. In general, system may include a plurality of stations through which samples and sample containers (e.g., flow cells) progress. This progression may be achieved in a number of ways including, for example, physical movement of the sample to different stations, physical movement of different stations to a sample, delivery of fluid from different stations to a sample such as via valve actuation or some combination thereof. A system may be designed for cyclic operation in which reactions are promoted with single nucleotides or with oligonucleotides, followed by flushing, imaging and de-blocking in preparation for a subsequent cycle, as indicated by reference numerals 496, 498 and 500. In a particular system, the samples may be circulated through a closed loop path for sequencing, synthesis, ligation, or any other suitable process. Again, it should be noted that the process illustrated is not necessarily limiting, and the present invention may allow data to be acquired from any suitable system employed for any application (e.g. image data, electrical data etc.).

In the illustrated embodiment, the nucleotide delivery operation 494 provides a process stream to the samples. An effluent stream from the flow cells may be discarded or, if desired, recaptured and recirculated in the nucleotide delivery system. In the illustrated embodiment, then, the sample container may be flushed in the flush operation 496 to remove additional reagents and to clarify the sample for imaging. The sample is then imaged or otherwise detected in the data capture operation 490 where data may be generated that may be analyzed for determination of the sequence of a progressively building nucleotide chain, such as based upon a template, or for any other analysis, depending again upon the nature of the molecules. In a presently contemplated embodiment, for example, an imaging system used for this operation may employ confocal line scanning to produce progressive pixilated image data that may be analyzed to locate individual sites in an array and to determine the type of nucleotide that was most recently attached or bound to each site. Other imaging techniques may also suitably be employed, such as techniques in which one or more points of radiation are scanned along the sample. Various embodiments of the systems and methods of the present disclosure are exemplified with respect to optical detection. It will be understood that other detection modes (e.g. non-optical detection) may be used. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified, for example, by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties).

Following the detection and data collection operation, then, the samples may progress to a de-blocking operation 500 in which a blocking molecule or protecting group is cleaved from the last added nucleotide, along with a marking dye. If the system is used for optically detected sequencing, by way of example, image data may be stored and forwarded to a data analysis system as indicated generally at reference numeral 484.

The analysis system will typically include a general purpose or application-specific programmed computer providing for user interface and automated or semi-automated analysis of the data to determine which of the four common DNA nucleotides was detected as a particular sequencing cycle (e.g. in the case of SBS, the identifying of the nucleotide that was last added at each of the sites of the array can be determined). As will be appreciated by those skilled in the art, in some embodiments such analysis may be performed based upon the color of unique tagging dyes for each of the four common DNA nucleotides. The data may be further analyzed by the downstream data analysis operations 502 and processing and data storage operations 504. In these operations, secondary data derived from the primary data may be stored, encoded, processed and analyzed. Due to the large volume of data collected, certain portions of the primary or secondary data may be compressed or discarded. Again, the sequencing application is intended to be one example only, and other operations, such as diagnostic applications, clinical applications, gene expression experiments, and so forth may be carried out that will generate similar data operated on by the present invention. Some examples of array based methods that generate image data that may be made and used in accordance with the teachings herein include, array-based genotyping or expression analyses. Such analyses may be carried out, for example, based on binding of a labeled target analyte to a particular probe of the microarray or due to a target-dependent modification of a particular probe to incorporate, remove, or alter a label at the probe location. Any one of several assays may be used to identify or characterize targets using a microarray as described, for example, in U.S. Patent Application Publication Nos. 2003/0108867 A1; 2003/0108900 A1; 2003/0170684 A1; 2003/0207295 A1; or 2005/0181394 A1, each of which is hereby incorporated by reference in its entirety. It is contemplated that the system, or various subcombinations of the exemplified system components, may include an interface designed to permit networking of the system to one or more detection systems acquiring image data (or other data) from biological microarrays of the type described. The interface may receive and condition data, where appropriate. In general, however, an imaging system will output digital image data representative of individual picture elements or pixels that, together, form an image of the biological microarray. One or more processors process the received image data in accordance with a plurality of routines defined by processing code. The processing code may be stored in various types of memory circuitry, and will include informatics routines for determining the nature of the molecules captured at each site of the array, and where desired, for determining possible structures comprising these (e.g., piecing the molecules together in longer, meaningful groups.

While only certain features of the contemplated embodiments have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for preparing a biological microarray, comprising:
providing an array of base pads at predetermined sites on a substrate, wherein individual base pads are configured to capture a nucleic acid molecule; and contacting the array of base pads with a mixture of different nucleic acid molecules under conditions wherein a nucleic acid molecule is captured at each base pad, wherein a porous attachment layer is disposed over the base pads such that the porous attachment layer at least partially covers the base pads and the porous attachment layer is configured to attach amplified copies of the nucleic acid molecules comprising nucleotides or nucleotide-like components.

2. The method of claim 1, wherein individual base pads are configured to capture no more than one nucleic acid molecule.

3. The method of claim 2, wherein a single nucleic acid molecule is captured by each and every base pad in the array.

4. The method of claim 2, wherein a single nucleic acid molecule is captured by fewer than all of the base pads in the array.

5. The method of claim 1, wherein the nucleic acid molecules comprise nucleotides or nucleotide-like components.

6. The method of claim 1, further comprising amplifying the single nucleic acid molecule at each base pad to obtain at each base pad a region comprising copies of the nucleic acid molecule, wherein the copies of the nucleic acid molecule are attached to the porous attachment layer.

7. The method of claim 1, wherein the substrate comprises a glass.

8. The method of claim 1, wherein the base pads comprise gold.

9. The method of claim 1, wherein the porous attachment layer is patterned.

10. The method of claim 9, wherein the porous attachment layer comprises a plurality of regions at least partially surrounding each of the base pads.

11. The method of claim 1, wherein the porous attachment layer extends substantially continuously over the plurality of base pads.

12. The method of claim 1, wherein the porous attachment layer comprises acrylamide.

13. The method of claim 1, wherein the porous attachment layer is a porous hydrogel.

14. A method for preparing a biological microarray, comprising:
    forming an array of base pads at predetermined sites on a substrate;
    disposing a molecule binding substance over each of the base pads, thereby configuring each of the base pads to capture a single nucleic acid molecule by linking the single nucleic acid molecule to the molecule binding substance; and
    disposing a porous attachment layer over the base pads such that the base pads are in between the porous attachment layer and the substrate, wherein the porous attachment layer is configured to attach copies of the nucleic acid molecule, and wherein the copies of the nucleic acid molecule are obtained through amplifying the single nucleic acid molecule at each base pad.

15. A method for preparing a biological microarray, comprising:
    forming a polymer layer on a substrate, wherein the polymer layer comprises a poly(N-(5-azidoacetamidylpentyl)acrylamide-co-acrylamide) polymer;
    disposing a photoresist layer over the polymer layer;
    forming interstitial spaces in the photoresist layer and the polymer layer; and
    removing the photoresist layer to expose polymer base pads, wherein the polymer base pads are coupled to a molecule binding substance.

16. A method for preparing a biological microarray, comprising:
    forming a polymer layer on a surface of a substrate;
    forming a plurality of spaced apart photoresist regions on the polymer;
    contacting exposed portions of the polymer layer with a plurality of primers; and
    removing the photoresist regions and covered portions of the polymer layer such that a plurality of spaced apart polymer pads coupled to the plurality of primers remain on the surface of the substrate.

17. A method for preparing a biological microarray, comprising:
    providing an array of base pads at predetermined sites on a substrate, wherein individual base pads are configured to capture a nucleic acid molecule and a porous attachment layer disposed over the base pads, and wherein the base pads are formed by an imprint lithographic process, the imprint lithographic process comprising: disposing a transfer layer on the substrate, disposing a light-curing resist layer over the transfer layer, patterning the resist layer via a mold, curing the patterned resist layer, etching the resist and transfer layers to expose regions of the substrate, depositing a pad-forming substance over the exposed regions of the substrate, and removing the resist and transfer layers.

18. The method of claim 17, wherein curing the patterned resist layer comprises exposing the mold to radiation to cure the patterned resist layer without removing the mold from the patterned resist layer.

* * * * *